US009555188B2

(12) United States Patent
Sarkinen et al.

(10) Patent No.: US 9,555,188 B2
(45) Date of Patent: Jan. 31, 2017

(54) IMPLANTABLE INFUSION DEVICE HAVING VOLTAGE BOOST CIRCUIT AND SELECTION CIRCUIT TO ALTERNATELY CONNECT BATTERY WITH CHARGING CIRCUIT

(75) Inventors: Scott A. Sarkinen, Greenfield, MN (US); Christopher Ambri, Mesa, AZ (US); Charles Randall Rogers, Maple Grove, MN (US); Naveed Alam, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 1287 days.

(21) Appl. No.: 13/458,150

(22) Filed: Apr. 27, 2012

(65) Prior Publication Data

US 2013/0289539 A1    Oct. 31, 2013

(51) Int. Cl.
*A61M 5/142* (2006.01)
*H02J 1/14* (2006.01)
*H02J 7/34* (2006.01)
*A61M 5/145* (2006.01)

(52) U.S. Cl.
CPC ........... *A61M 5/14276* (2013.01); *H02J 1/14* (2013.01); *H02J 7/345* (2013.01); *A61M 5/1452* (2013.01); *A61M 2205/8206* (2013.01); *A61M 2205/8212* (2013.01)

(58) Field of Classification Search
CPC .............. A61M 5/142; A61M 5/1452; A61M 2205/8206; A61M 2205/8212; H02M 3/07; A61N 1/325; A61N 1/0448; A61N 1/30; A61N 1/323; A61N 1/0428
USPC .................................................. 604/891.1
See application file for complete search history.

(56) References Cited

U.S. PATENT DOCUMENTS

| | | | | |
|---|---|---|---|---|
| 4,745,923 A | * | 5/1988 | Winstrom | 607/9 |
| 5,968,083 A | * | 10/1999 | Ciciarelli et al. | 607/62 |
| 6,308,101 B1 | * | 10/2001 | Faltys et al. | 607/57 |
| 6,479,970 B2 | * | 11/2002 | Reddy | 320/162 |
| 7,070,577 B1 | * | 7/2006 | Haller et al. | 604/131 |
| 7,545,658 B2 | * | 6/2009 | Thiele et al. | 363/60 |
| 7,927,326 B2 | * | 4/2011 | Sarkinen et al. | 604/891.1 |

(Continued)

OTHER PUBLICATIONS

High Current Pulse Generator. Iowa State Electrical Engineering Senior Design Project. p. 5. Accessed online Mar. 14, 2016. http://seniord.ece.iastate.edu/dec1306/uploads/1/8/1/8/18188693/dec13-06_design_doc_v2.pdf.*

(Continued)

*Primary Examiner* — Bhisma Mehta
*Assistant Examiner* — Matthew A Engel
(74) *Attorney, Agent, or Firm* — Harness, Dickey & Pierce, P.L.C.

(57) ABSTRACT

An implantable infusion device includes a pump, a charge storage unit, and a charging circuit configured to supply current to the charge storage unit from a battery in preparation for actuating the pump. The implantable infusion device also includes a pump actuator circuit configured to actuate the pump using energy from the charge storage unit, and a voltage boost circuit configured to provide a boosted battery voltage generated from the battery. The charging circuit is configured to supply current to the charge storage unit from the voltage boost circuit instead of directly from the battery in response to (i) a comparison of a voltage of the battery with a predetermined threshold and (ii) a comparison of a voltage of the charge storage unit with the voltage of the battery.

26 Claims, 18 Drawing Sheets

(56) References Cited

U.S. PATENT DOCUMENTS

| | | | |
|---|---|---|---|
| 7,999,604 B2* | 8/2011 | Jeong et al. | 327/536 |
| 8,246,573 B2* | 8/2012 | Ali et al. | 604/65 |
| 8,483,802 B2 | 7/2013 | Kalpin et al. | |
| 2002/0016568 A1* | 2/2002 | Lebel et al. | 604/131 |
| 2002/0058906 A1* | 5/2002 | Lebel et al. | 604/65 |
| 2002/0087114 A1* | 7/2002 | Hartlaub | 604/65 |
| 2003/0199855 A1* | 10/2003 | Rogers et al. | 604/891.1 |
| 2007/0040449 A1* | 2/2007 | Spurlin et al. | 307/64 |
| 2007/0052395 A1* | 3/2007 | Belch | 323/222 |
| 2008/0267796 A1* | 10/2008 | Sarkinen et al. | 417/411 |
| 2008/0269724 A1* | 10/2008 | Sarkinen et al. | 604/891.1 |
| 2010/0023095 A1* | 1/2010 | Stevenson et al. | 607/63 |
| 2010/0204766 A1* | 8/2010 | Zdeblick et al. | 607/119 |
| 2011/0264006 A1* | 10/2011 | Ali et al. | 600/587 |
| 2011/0280737 A1* | 11/2011 | Sarkinen et al. | 417/44.1 |
| 2012/0109099 A1* | 5/2012 | Rogers et al. | 604/500 |
| 2013/0289538 A1 | 10/2013 | Rogers et al. | |
| 2013/0289539 A1* | 10/2013 | Sarkinen et al. | 604/891.1 |

OTHER PUBLICATIONS

International Search Report and Written Opinion mailed Aug. 23, 2013 for PCT/US2013/037593, claiming benefit of U.S. Appl. No. 13/458,147, filed Apr. 27, 2012.
Pylarinos, Louis "Charge Pumps: An Overview" (2003) University of Toronto, http://citeseerx.ist.psu.edu/viewdoc/versions?doI=10.1.1.128.4085.
U.S. Appl. No. 13/458,147, filed Apr. 27, 2012, Rogers et al.

\* cited by examiner

IMPLANTABLE INFUSION DEVICE HAVING VOLTAGE BOOST CIRCUIT AND SELECTION CIRCUIT TO ALTERNATELY CONNECT BATTERY WITH CHARGING CIRCUIT

CROSS-REFERENCE TO RELATED APPLICATIONS

This application is related to U.S. patent application Ser. No. 13/458,147, filed Apr. 27, 2012. The disclosure of the above application is incorporated herein by reference in its entirety.

FIELD

The present disclosure relates to electrical systems for an implantable drug pump and more specifically to power management systems for a piston-based implantable infusion pump.

BACKGROUND

Implantable drug pumps allow drug therapies to be administered to a patient outside of a clinical setting. Smaller amounts of the drug can therefore be administered over long periods of time. In addition, implantable infusion pumps may inject drugs into areas such as the intrathecal space surrounding the spinal cord, where a drug is much more effective. For example, when administering a drug such as morphine intravenously instead of orally, only one-third of that drug may be needed. In other words, the drug is three times as effective when administered intravenously. Morphine may generally be ten times as effective when administered epidurally as compared to intravenously. Further, such a drug may be ten times as effective when being administered intrathecally as compared to epidurally.

Because an implantable drug pump is surgically implanted, the operating life of the implanted device needs to be as long as possible. Referring now to FIG. 1, an example implantable infusion device 100 is shown. The device 100 includes a reservoir 104 holding the drug to be administered. A pump 108 pumps drug from the reservoir 104 into the patient's body. A control circuit 112 drives the pump 108 and is powered by a battery 116.

The operating life of the device 100 may be governed by factors including the amount of drug stored in the reservoir 104 and the dosage rate, the life of the battery 116, and the mechanical longevity of the pump 108. In various implementations, the reservoir 104 may be replenished with additional quantities of the drug while the device 100 remains implanted in a patient. In such implementations, the battery 116 is even more important in determining the lifetime of the device 100. Improving battery life may allow implanted devices to be replaced less often.

SUMMARY

An implantable infusion device includes a pump, a charge storage unit, and a charging circuit configured to supply current to the charge storage unit from a battery in preparation for actuating the pump. The implantable infusion device also includes a pump actuator circuit configured to actuate the pump using energy from the charge storage unit, and a voltage boost circuit configured to provide a boosted battery voltage generated from the battery. The charging circuit is configured to supply current to the charge storage unit from the voltage boost circuit instead of directly from the battery in response to (i) a comparison of a voltage of the battery with a predetermined threshold and (ii) a comparison of a voltage of the charge storage unit with the voltage of the battery.

In other features, the pump comprises a piston and a solenoid coil, and the pump actuator circuit is configured to supply a current to the solenoid coil from the charge storage unit. The predetermined threshold is controlled in response to a firmware setting. The comparison of a voltage of the charge storage unit with the voltage of the battery includes comparing the voltage of the charge storage unit to a predetermined percentage of the voltage of the battery. The predetermined percentage is controlled in response to a firmware setting. A charge monitor circuit is configured to generate a signal in response to a comparison of the voltage of the charge storage unit with a predetermined level. The pump actuator circuit is enabled based on the signal.

In further features, the charging circuit is configured to decrease the current supplied to the charge storage unit in response to the voltage of the battery decreasing below a second predetermined threshold that is less than the predetermined threshold. In response to the voltage of the battery decreasing below the second predetermined threshold, the charging circuit is configured to halt supplying current to the charge storage unit. After halting supplying current to the charge storage unit, the charging circuit is configured to begin supplying increasing levels of current to the charge storage unit and verifying that the voltage of the battery does not decrease below the second predetermined threshold.

In still other features, the implantable infusion device includes a voltage rail that is selectively connected to the battery. A hold monitor circuit is configured to monitor a voltage of the voltage rail and, in response to the voltage of the voltage rail decreasing below a first threshold, activate the voltage boost circuit. An isolation circuit isolates the voltage rail from the voltage of the battery in response to a difference between the voltage of the battery and the voltage of the voltage rail. In response to the voltage of the voltage rail decreasing below the first threshold, the hold monitor circuit connects the boosted battery voltage to the voltage rail. In response to the voltage of the voltage rail increasing above a second threshold that is greater than the first threshold, the hold monitor circuit disconnects the boosted battery voltage from the voltage rail and deactivates the voltage boost circuit.

In other features, a boost control circuit is configured to (i) control the voltage boost circuit and (ii) inhibit operation of the charging circuit while the voltage boost circuit is starting. The boost control circuit is configured to inhibit operation of an alarm circuit and a telemetry circuit while the voltage boost circuit is starting. An electronic port finder circuit is powered by the charging circuit. The charging circuit is configured such that supplying current to the charge storage unit is mutually exclusive with powering the electronic port finder circuit.

In further features, an alarm circuit is configured to generate an audible alarm, and the alarm circuit is powered by the voltage boost circuit. The alarm circuit disables the charging circuit while the alarm circuit is generating the audible alarm. A telemetry circuit communicates with an external device. Operation of the telemetry circuit is inhibited while the voltage boost circuit is starting. The telemetry circuit is configured to shut down in response to the voltage of the battery decreasing below a second predetermined threshold that is less than the predetermined threshold.

A method of operating an implantable infusion device includes supplying current from a battery to a charge storage unit in preparation for a cycle of a pump, and selectively actuating the pump using energy from the charge storage unit. The method includes performing a first comparison of a voltage of the battery with a predetermined threshold and performing a second comparison of a voltage of the charge storage unit with the voltage of the battery. The method includes determining whether a boosted battery voltage is required in response to the first comparison and the second comparison, and when the boosted battery voltage is required, generating the boosted battery voltage and supplying current to the charge storage unit from the boosted battery voltage instead of directly from the battery.

In other features, the pump comprises a piston and a solenoid coil, and the method further comprising supplying a current to the solenoid coil from the charge storage unit to actuate the pump. The predetermined threshold is controlled in response to a firmware setting. The second comparison includes comparing the voltage of the charge storage unit to a predetermined percentage of the voltage of the battery. The predetermined percentage is controlled in response to a firmware setting. The method also includes generating a signal in response to a comparison of the voltage of the charge storage unit with a predetermined level, and selectively actuating the pump in response to the signal.

In further features, the method includes decreasing the current supplied to the charge storage unit in response to the voltage of the battery decreasing below a second predetermined threshold that is less than the predetermined threshold. The method also includes, in response to the voltage of the battery decreasing below the second predetermined threshold, decreasing the current to the charge storage unit to zero. The method also includes incrementally supplying greater levels of current to the charge storage unit subsequent to decreasing the current to zero; and verifying that the voltage of the battery does not decrease below the second predetermined threshold while supplying the greater levels of current.

In still other features, the method includes selectively connecting a voltage rail to the battery, monitoring a voltage of the voltage rail, and generating the boosted battery voltage in response to the voltage of the voltage rail decreasing below a first threshold. The method also includes isolating the voltage rail from the voltage of the battery in response to a difference between the voltage of the battery and the voltage of the voltage rail. The method also includes, in response to the voltage of the voltage rail decreasing below the first threshold, connecting the boosted battery voltage to the voltage rail. The method also includes, in response to the voltage of the voltage rail increasing above a second threshold that is greater than the first threshold, disconnecting the boosted battery voltage from the voltage rail and halting generation of the boosted battery voltage.

In other features, the method also includes inhibiting the supplying of current to the charge storage unit while generation of the boosted battery voltage is beginning. The method also includes operating an electronic port finder function mutually exclusively with supplying current to the charge storage unit. The method also includes generating an audible alarm powered by the boosted battery voltage. The method also includes inhibiting generation of the audible alarm while generation of the boosted battery voltage is beginning. The method also includes inhibiting the supplying of current to the charge storage unit while the audible alarm is being generated. The method also includes inhibiting communication with an external device while generation of the boosted battery voltage is beginning. The method also includes shutting down communication with the external device in response to the voltage of the battery decreasing below a second predetermined threshold that is less than the predetermined threshold.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

An infusion device according to the principles of the present disclosure may use a solenoid-operated piston pump for pumping a drug to a patient instead of a miniature stepper motor as used in previous systems. While the miniature stepper motor had a peak current demand of, for example, 5 milliamps, a piston pump may have a higher peak current demand, such as 0.5 amps. The difference between those peak current demands is two orders of magnitude, creating a much more difficult current draw for a battery to source.

In addition, battery chemistry may cause the battery to have a large series resistance, and the infusion device may include many loads on the battery, such as pump cap charge, alarm, telemetry and electronic port finding. Further, there may be minimal voltage headroom between the required operating voltage of various components and the voltage provided by the battery, especially as the battery output decreases over time.

As a result, the present disclosure describes a variety of approaches, including exclusivity, interleaving, and duty-cycling, to maximize battery life, minimize voltage droop, and allow a range of demands to be met by a single battery. For example, regulators may require a certain input level to allow the output to be regulated. When the supply voltage dips below that level, the output voltage is no longer regulated and may simply track the battery voltage. In addition, telemetry and digital logic may require a certain voltage level to operate deterministically. The following description presents solutions to satisfy these requirements while still providing a large current to actuate a piston solenoid.

Figure 1:
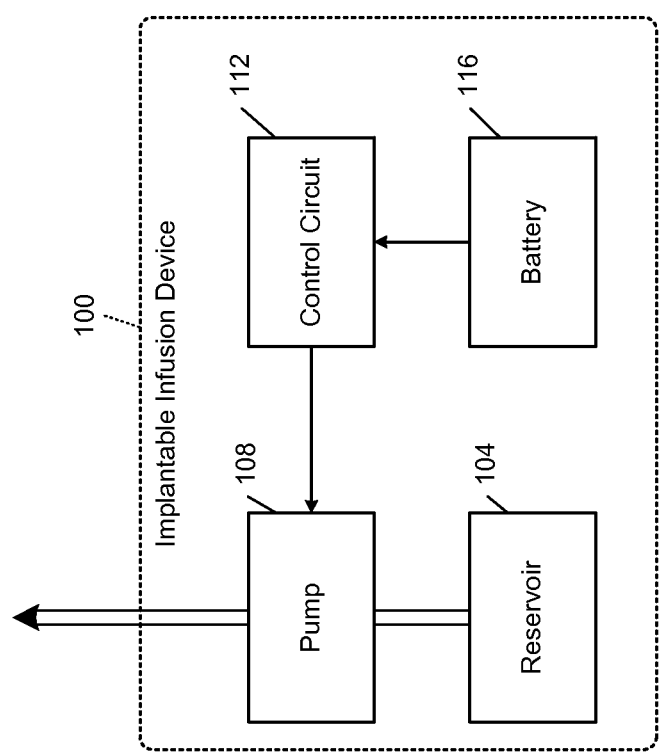
FIG. 1 is a functional block diagram of an implantable infusion device according to the prior art.
Figure 2:
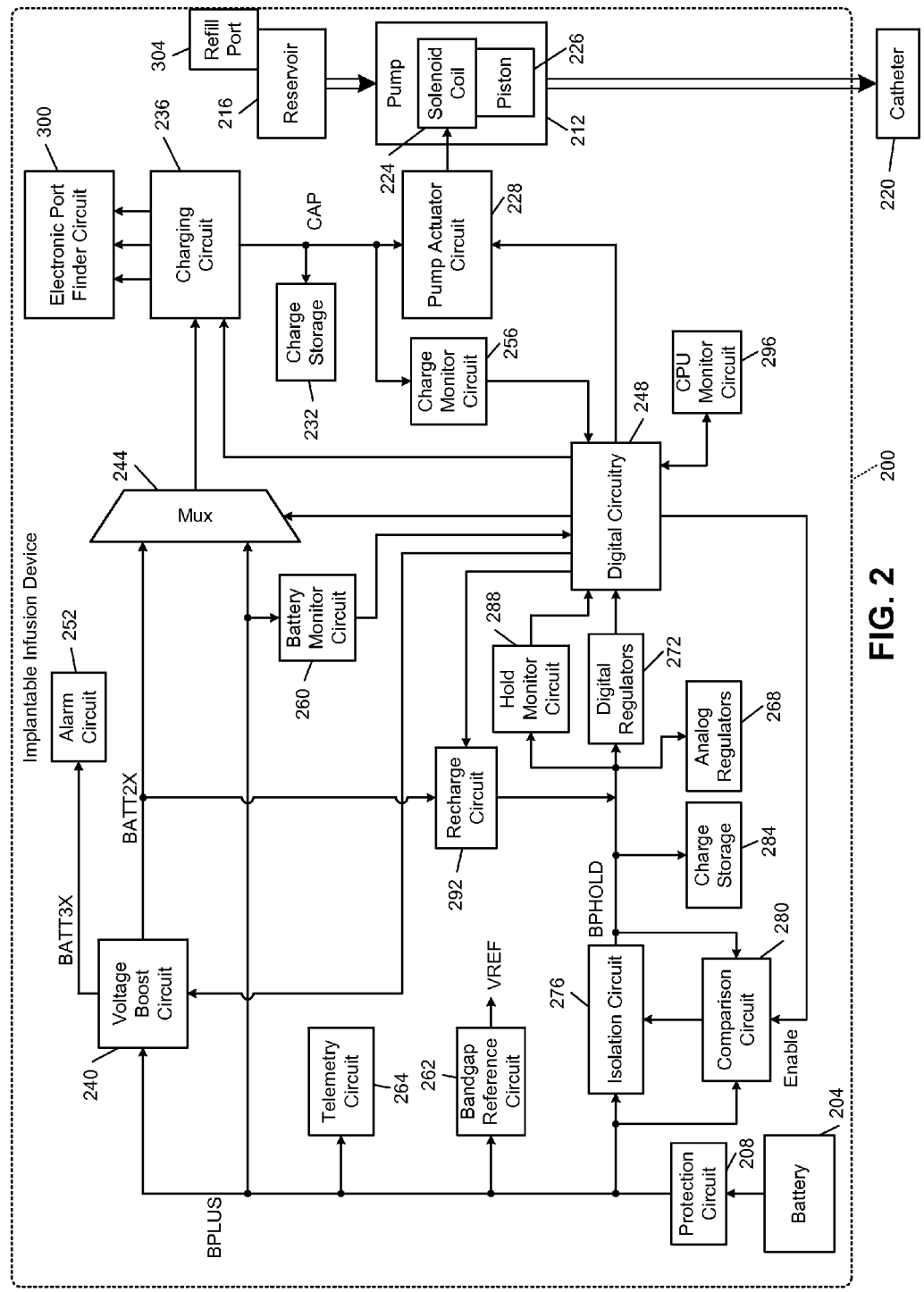
FIG. 2 is a functional block diagram of an example implantable infusion device according to the principles of the present disclosure.

Referring now to FIG. 2, an example implantable infusion device 200 includes a battery 204, whose output is connected to a protection circuit 208. The protection circuit may limit the amount of current supplied by the battery 204 to prevent undesirable heat increases from excessively high current draw such as may be caused by a short circuit. An output of the protection circuit 208 is referred to as BPLUS, which is functionally the battery voltage for the remainder of the implantable infusion device 200.

A pump 212 delivers amounts of drug from a reservoir 216 to a catheter 220. The implantable infusion device 200 may be implanted in an abdominal cavity of a patient and the catheter 220 provides the drug to an intrathecal space or an epidural space of the patient. The pump 212 includes a solenoid coil 224, which is energized by a pump actuator circuit 228. Energizing the solenoid coil 224 moves a piston 226, which mechanically forces an amount of the drug into the catheter 220. A portion of the piston 226 may be an armature surrounded by the solenoid coil 224.

The pump actuator circuit 228 may energize the solenoid coil 224 from a voltage rail labeled CAP. The CAP voltage rail is supported by charge storage 232. The charge storage 232 may include one or more capacitors in parallel, such as a bank of four capacitors totaling four thousand microfarads.

The pump actuator circuit 228 may energize the solenoid coil 224 once the voltage of the CAP voltage rail has reached a predetermined voltage. For example, this predetermined voltage may be 2.8 V. A charging circuit 236 supplies current to the charge storage 232. Although the charge storage 232 is not limited to capacitors, for ease of explanation, delivering charge to the charge storage 232 will be referred to in this application as charging the capacitor 232.

At various times, the voltage to which the CAP voltage rail is desired to be charged is close to or even greater than the battery voltage BPLUS. In those situations, the voltage boost circuit 240 provides an increased voltage, labeled in FIG. 2 as BATT2X. BATT2X and BPLUS are received by a multiplexer circuit 244. Digital circuitry 248 selects either BPLUS or BATT2X to be provided to the charging circuit 236. By boosting BPLUS, the charging circuit 236 has enough voltage headroom to charge the capacitor 232 to the desired voltage.

In various implementations, the voltage boost circuit 240 may include a voltage doubler and/or a voltage tripler. Although the output of the voltage boost circuit 240 is labeled BATT2X, the voltage boost circuit 240 is not limited to only doubling the voltage BPLUS. The voltage boost circuit 240 may boost the voltage BPLUS by other factors, and may provide more than one boost level. The voltage boost circuit 240 may be referred to as a DC-DC converter, and may be implemented using one or more charge pumps.

An alarm circuit 252 is also powered from the voltage boost circuit. In various implementations, the alarm circuit 252 may be powered by a voltage, BATT3X, that is higher than BATT2X. For example, BATT3X may be approximately equal to three times BPLUS. The voltage boost circuit 240 may produce BATT2X and BATT3X mutually exclusively. In various implementations, the alarm circuit 252 may drive the alarm (not shown) with out-of-phase signals, both having voltage swings between zero and approximately BATT3X. If the out-of-phase signals are connected to the alarm with reverse polarity, the total voltage swing seen by the alarm may be approximately two times BATT3X. In this manner, the peak-to-peak voltage across the alarm may be, for example, approximately six times BPLUS.

The alarm circuit 252 generates an alarm that can be used to signal an event, such as an approaching end of life of the battery 204, or a problem with the pump 212. In various implementations the alarm circuit 252 can provide feedback to indicate that transmitted information, such as a new dosing schedule, has been received by the implantable infusion device 200. The alarm circuit 252 can also signal events, such as the beginning of a bolus.

The alarm circuit 252 is made to be perceptible to the patient and may also be made to be perceptible to third parties, which may be relevant in a clinical setting or if the patient is incapacitated. For example, the alarm circuit 252 may include an audible alarm and/or a vibratory alarm.

A charge monitor circuit 256 monitors the voltage on the CAP voltage rail, which the digital circuitry 248 uses to determine when there is sufficient voltage for the pump actuator circuit 228 to energize the solenoid coil 224. The charge monitor circuit 256 may also determine when the voltage of the CAP voltage rail is close enough to BPLUS that voltage boosting is necessary to effectively continue charging the capacitor 232.

A battery monitor circuit 260 monitors BPLUS and determines whether BPLUS falls below various thresholds during various operating conditions. These determinations may be acted upon by digital circuitry 248. For example, while charging the capacitor 232, the battery monitor circuit 260 may generate a trip signal when BPLUS decreases below a first threshold. This trip signal may be used to activate the voltage boost circuit 240. The first threshold may be derived from a reference voltage generated by a reference such as a bandgap reference circuit 262.

When either charging is occurring or a telemetry circuit 264 is operating, the battery monitor circuit 260 may compare BPLUS to a second threshold. If BPLUS decreases below that threshold, charging of the charge storage 232 may be slowed, paused, or halted. Further, when telemetry is operating, the battery monitor circuit 260 may compare BPLUS to a third threshold and if BPLUS decreases below that third threshold, the battery monitor circuit 260 may signal that telemetry should be shut down until BPLUS recovers. The telemetry circuit 264 allows communication to and/or from the implantable infusion device 200, such as with an external programmer or data logger.

To provide a relatively stable voltage supply to various components, such as analog regulators 268 and digital regulators 272, a voltage rail labeled BPHOLD is used. The digital regulators 272 may provide a regulated voltage to the digital circuit 248. BPHOLD is selectively connected to BPLUS by isolation circuit 276. The isolation circuit 276 disconnects BPHOLD from BPLUS in response to a comparison circuit 280. The comparison circuit 280 may instruct the isolation circuit 276 to disconnect BPHOLD from BPLUS when BPLUS is not at least a predetermined voltage greater than BPHOLD. For example only, the comparison circuit 280 may isolate BPHOLD from BPLUS when BPLUS is not at least twenty millivolts greater than BPHOLD. Digital circuitry 248 may be configured to selectively disable the comparison circuit 280, thereby causing the isolation circuit 276 to disconnect BPHOLD from BPLUS regardless of what is measured by the comparison circuit 280.

The voltage of BPHOLD is maintained by charge storage 284. The charge storage 284 may include one or more capacitors, which may total, for example, one hundred microfarads. A hold monitor circuit 288 monitors the voltage of BPHOLD and generates a BPHOLD_High signal when the voltage of BPHOLD exceeds a threshold. Similarly, the hold monitor circuit 288 may generate a BPHOLD_Low signal when the voltage of BPHOLD decreases below a second threshold. In response to the BPHOLD_Low signal being generated, the digital circuitry 248 may activate the voltage boost circuit 240, which supplies boosted voltage to BPHOLD via a recharge circuit 292.

The current from the voltage boost circuit 240 will charge the charge storage 284 until the hold monitor circuit 288 generates the BPHOLD_High signal, at which point the recharge circuit 292 turns off. The digital circuitry 248 may then also turn off the voltage boost circuit 240. The charge storage 284 then supplies current to loads on the BPHOLD rail, causing the voltage to decrease to BPHOLD_Low, at which point the recharge cycle starts again. A CPU monitor circuit 296 monitors a processor voltage and may inform the digital circuitry 248 of a result of a comparison of the processor voltage with a threshold.

Alternatively to providing current to the charge storage 232, the charging circuit 236 may power an electronic port finder circuit 300. The electronic port finder circuit 300 may provide electromagnetic signals that allow a refill operation to accurately locate a refill port 304 on the reservoir 216. The charging circuit 236 may supply current to each of three locating coils of the electronic port finder circuit 300. The electromagnetic field created by the locating coils is used by a location apparatus during a refill procedure.

Figure 3:
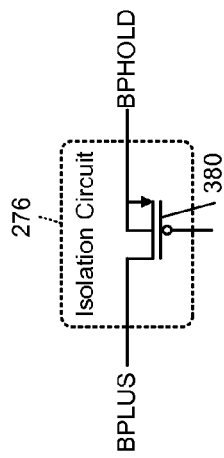
FIG. 3 is a schematic of an example implementation of a protection circuit.

Referring now to FIG. 3, an example implementation of the protection circuit 208 may simply include a resistor 320. The resistance of the resistor 320 may be chosen to satisfy a temperature rise constraint in the event of a short circuit. In other words, the resistance value of the resistor 320 may be set to limit the amount of current flowing in a short circuit to a level that will cause the temperature of the implantable infusion device 200 to rise at a lower rate than the specified temperature rise rate. For example only, the resistance value may be 10 ohms. In various other implementations, the protection circuit 208 may be implemented using an active circuit that controls and limits current in the event of a short circuit. When no short circuit is present, the active circuit may present a very low resistance to current flow from the battery 204.

Figure 4:
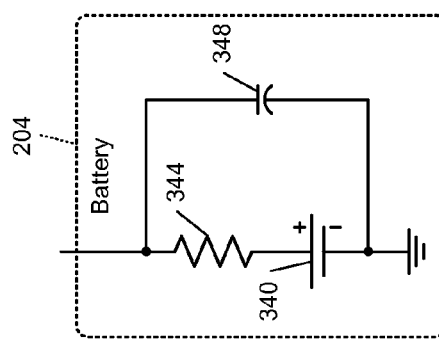
FIG. 4 is a schematic of an example equivalent circuit of a battery.

Referring now to FIG. 4, an equivalent schematic of the battery 204 is shown. The electrochemical cells produce a DC voltage 340, which for example may start out at approximately 3.1 V and decrease over time to approximately 2.6 V or less. Intrinsic resistance of the battery may be modeled as series resistor 344. For example only, the resistor 344 may have a resistance value between thirty-five ohms and seventy-five ohms. A capacitor 348 may be added to provide capacity for current inrush events. For example, the capacitor 348 may have a capacitance of twenty-two microfarads.

Figure 5:
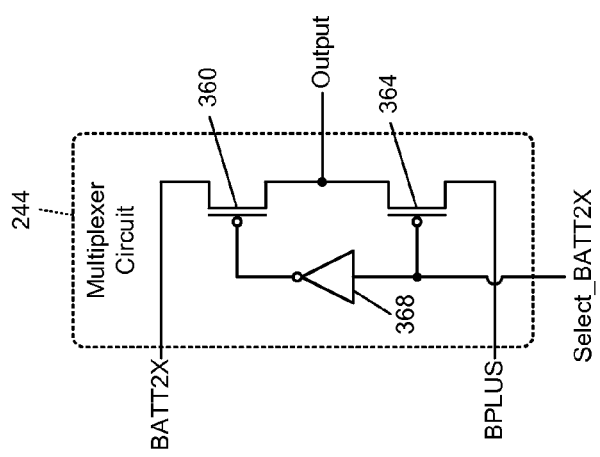
FIG. 5 is a schematic of an example implementation of a multiplexer circuit.

Referring now to FIG. 5, an example implementation of the multiplexer circuit 244 is shown. BATT2X is received at a first terminal of a transistor 360, while BPLUS is received at a first terminal of transistor 364. Second terminals of the transistors 360 and 364 are connected to each other and are output from the multiplexer circuit 244. A control terminal of the transistor 364 is connected to a select input, which may be received from the digital circuitry 248. In various implementations, the select input may be an active-high BATT2X select signal—i.e., when the select signal is high, BATT2X is selected by the multiplexer circuit 244. An inverter 368 inverts the select signal and provides the inverted select signal to a control terminal of the transistor 360. Level shifters may be used, for example, to scale the output of the inverter 368 to the BATT2X voltage level. This prevents insufficient voltages from causing unwanted operation: for example, if the control terminal of the transistor 360 falls below BATT2X, the transistor 360 will begin to turn on.

In various implementations, the transistors 360 and 364 may be p-channel metal oxide semiconductor field effect transistors (MOSFETs). Well switches (not shown) may be connected across each of the transistors 360 and 360 to ensure that the body voltages are always connected to the highest terminal potential in order to keep the well diodes from becoming forward biased and turning on.

Figure 6:
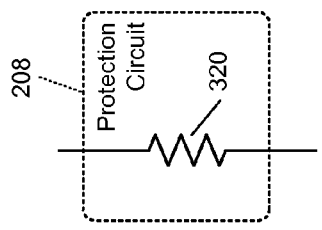
FIG. 6 is a schematic of an example implementation of a isolation circuit.

Referring now to FIG. 6, the isolation circuit 276 may be implemented using a transistor 380 whose control terminal is controlled by the comparison circuit 280 of FIG. 2. First and second terminals of the transistor 380 are connected to BPLUS and BPHOLD, respectively. In the implementation shown, the transistor 380 is a p-channel MOSFET and a body of the transistor 380 is connected to BPHOLD.

Figure 7:
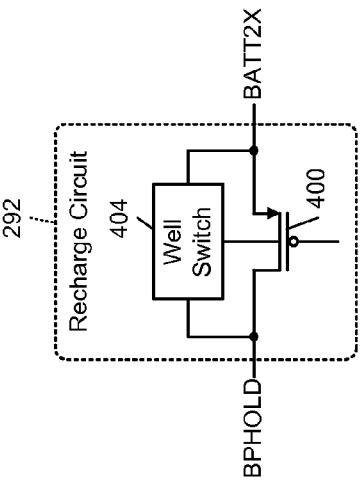
FIG. 7 is a schematic of an example implementation of a recharge circuit.

Referring now to FIG. 7, an example implementation of the recharge circuit 292 includes a transistor 400 whose control terminal is controlled by the digital circuitry 248. First and second terminals of the transistor 400 are connected to BPHOLD and BATT2X, respectively. A well switch 404 is connected to BPHOLD, BATT2X, and a body of the transistor 400.

Figure 8:
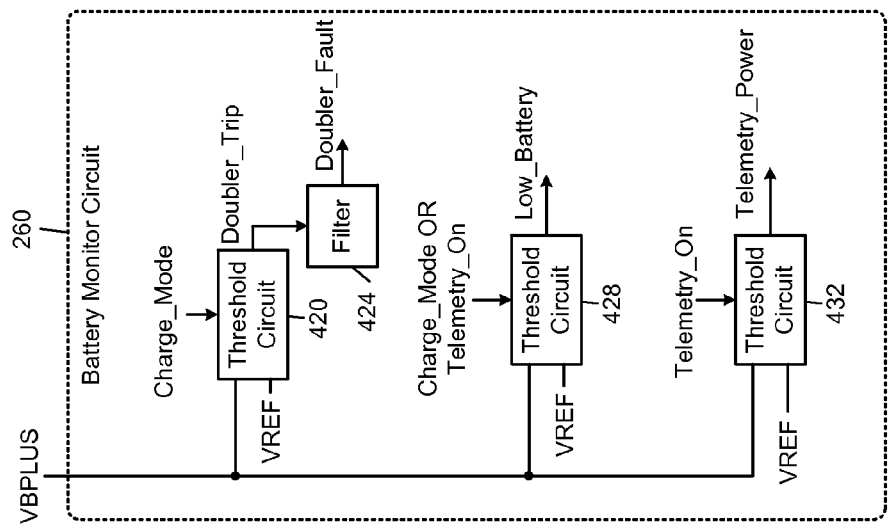
FIG. 8 is a block diagram of an example implementation of a battery monitor circuit.

Referring now to FIG. 8, an example implementation of the battery monitor circuit 260 is shown. A threshold circuit 420 compares BPLUS to a reference voltage and outputs a Doubler_Trip signal in response to the comparison. To save power, the threshold circuit 420 may only operate at certain times, such as when a charging mode is activated as indicated by the Charge_Mode signal. The charging mode is enabled when the charging circuit 236 is charging the capacitor 232 in preparation for actuating the pump 212.

Figure 10:
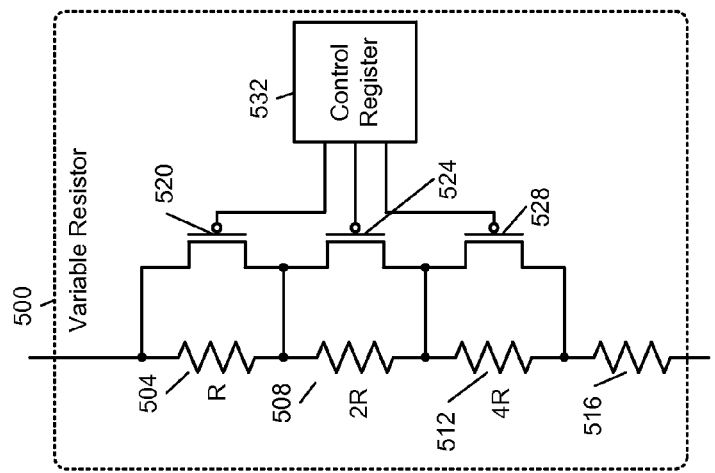
FIG. 10 is a schematic of an example implementation of a variable resistor.
Figure 9:
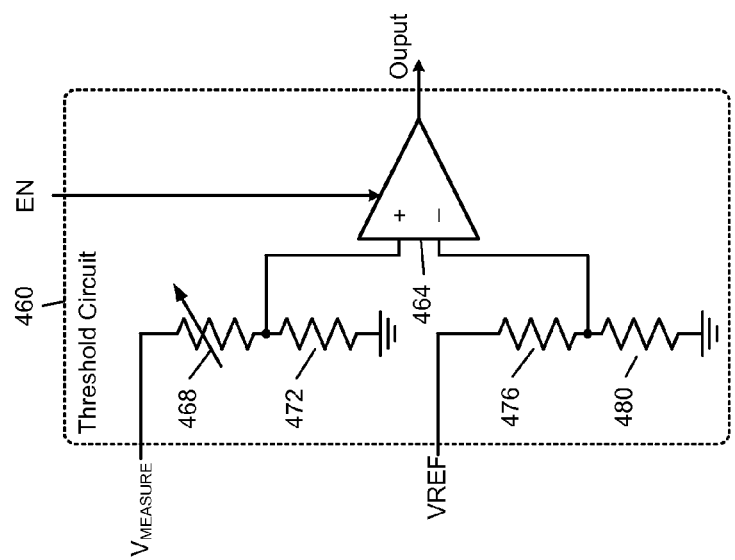
FIG. 9 is a schematic of an example implementation of a threshold circuit.

The Doubler_Trip signal may be operated on by a filter 424. For example only, the filter 424 may determine when the Doubler_Trip signal is asserted for at least a predetermined period of time, at which point the filter 424 outputs a Doubler_Fault signal. In other words, the filter 424 removes glitches of the Doubler_Trip signal that are shorter than the predetermined period of time. In various implementations, the predetermined period of time may be twenty milliseconds. The threshold circuit 420 may allow an adjustable threshold to be set, such as is shown in FIGS. 9 and 10. For example only, the threshold circuit 420 may allow VBPLUS to be compared to a voltage within the range of 2.2 V to 2.45 V. The Doubler_Fault signal may cause the voltage boost circuit 240 of FIG. 2 to be activated.

A threshold circuit 428 compares VBPLUS to VREF when either telemetry is on, as indicated by the Telemetry_On signal, or the charge mode is enabled. In response to this comparison, a Low_Battery signal is generated. For example only, the Low_Battery signal may be generated when VBPLUS is less than a predetermined voltage, which for example can be set within the range of 1.9 V to 2.1 volts. The Low_Battery signal may cause charging of the capacitor 232 to be slowed, paused, or halted.

A threshold circuit 432 compares VBPLUS to a reference voltage when the Telemetry_On signal is present and in response, generates a Telemetry_Power signal. For example, the threshold circuit 432 generates the Telemetry_Power signal when VBPLUS is less than the voltage in a range of 1.8 V to 1.9 V. The Telemetry_Power signal may be used to turn off and/or reset the telemetry circuit 264 of FIG. 2.

Referring now to FIG. 9, an example implementation of a threshold circuit 460 is shown. The threshold circuit 460 may be implemented in one or more of the threshold circuits 420, 428, and 432 of FIG. 8. The threshold circuit 460 includes an operational amplifier (opamp) 464 that operates only when an enable signal EN is present. The opamp 464 has a non-inverting input that receives a voltage from a node of a first voltage divider connected to a voltage to be measured, $V_{MEASURE}$. An inverting input of the opamp 464 is connected to a node of a second voltage divider, which is connected to a reference voltage, such as from the bandgap reference circuit 262.

The first voltage divider includes a resistor 468 and a resistor 472. Although FIG. 9 shows that the resistor 468 is a variable resistor, either, both, or none of the resistors 468 and 472 may be variable. When the same voltage is going to be measured by multiple threshold circuits including the threshold circuit 460, the first voltage divider may be shared between the threshold circuits. The second voltage divider includes a resistor 476 and a resistor 480. In various implementations, either, both, or none of the resistors 476 and 480 may be variable resistors.

Referring now to FIG. 10, one example implementation of a variable resistor 500 is shown. For example only, the variable resistor 500 may be used to implement any of the resistors 468, 472, 476, and 480 in FIG. 9. The variable resistor 500 includes fixed resistors 504, 508, 512, and 516 in series. Transistors 520, 524, and 528 selectively short circuit the resistors 504, 508, and 512, respectively.

The transistors 520, 524, and 528 are controlled by a control register 532. The value stored by the control register 532 can therefore set the total resistance of the variable resistor 500. Although three switchable resistors are shown in FIG. 10, more or fewer may be used in any given implementation of a variable resistor. The resistor 516, which is not switchable, is included in FIG. 10 to offset the possible values of resistance. Therefore, even if the control register 532 causes each of the resistors 504, 508, and 512 to be short circuited, the variable resistor 500 will still have the resistance of the resistor 516. To afford the maximum range of control, the resistors 504, 508, and 512, may have a binary relationship: for example, the resistor 508 has a resistance value twice that of the resistor 504 and the resistor 512 has a resistance value twice that of the resistor 508.

Figure 11:
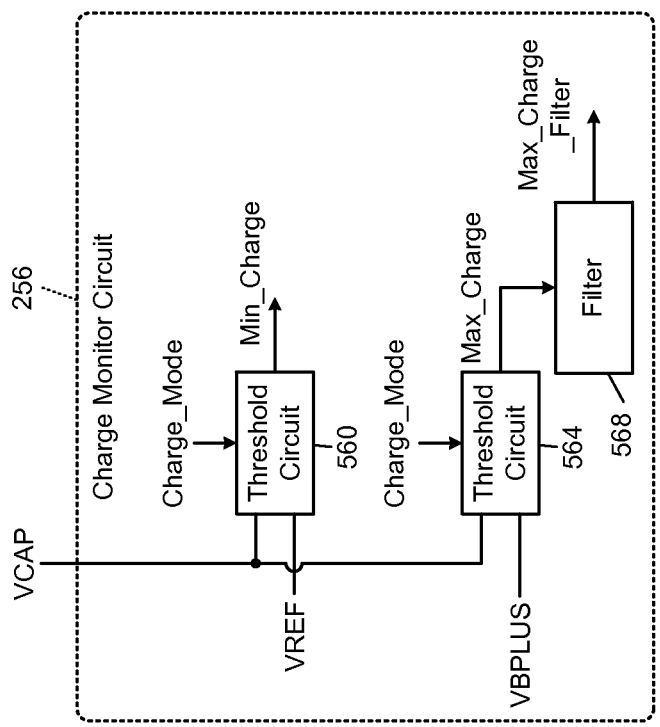
FIG. 11 is a block diagram of an example implementation of a charge monitor circuit.

Referring now to FIG. 11, an example implementation of the charge monitor circuit 256 is shown. A threshold circuit 560 compares the voltage, VCAP, of the CAP voltage rail to a reference voltage when the Charge_Mode signal is present. The threshold circuit 560 generates a Min_Charge signal when VCAP is greater than the reference voltage, such as a voltage in the range of 2.7 V to 2.9 V.

A threshold circuit 564 compares VCAP to VBPLUS when the Charge_Mode signal is present. For example, the threshold circuit 564 generates a Max_Charge signal when VCAP is greater than a predetermined percentage of VBPLUS. The predetermined percentage may be variable within a range, such as between 92 percent and 99 percent. A filter 568 may output a Max_Charge_Filter signal in response to the Max_Charge signal being present for at least a predetermined period of time. For example only, the predetermined period of time may be twenty milliseconds.

The Max_Charge_Filter signal indicates that VCAP is getting too close to VBPLUS and therefore the voltage boost circuit 240 should be enabled to continue charging the capacitor 232. The Min_Charge signal indicates that the minimum level of charging necessary for actuating the pump 212 has been achieved and therefore the pump can be actuated.

Figure 12:
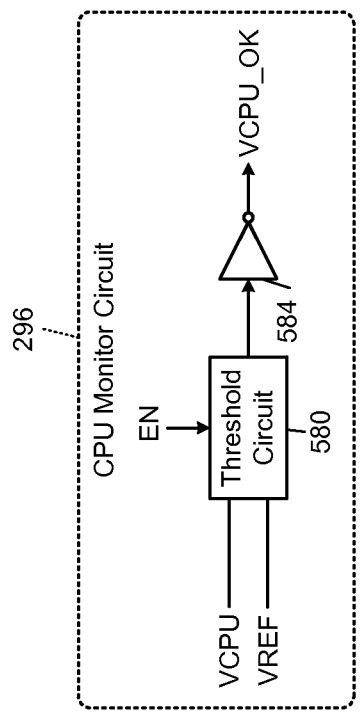
FIG. 12 is a block diagram of an example implementation of a CPU monitor circuit.

Referring now to FIG. 12, an example implementation of the CPU monitor circuit 296 is shown. A threshold circuit 580 compares a CPU voltage to a reference voltage based on an enable signal. For example, the enable signal may be controlled by a firmware register. An inverter 584 inverts an output of the threshold circuit 580 and outputs a VCPU_OK signal.

Figure 13B:
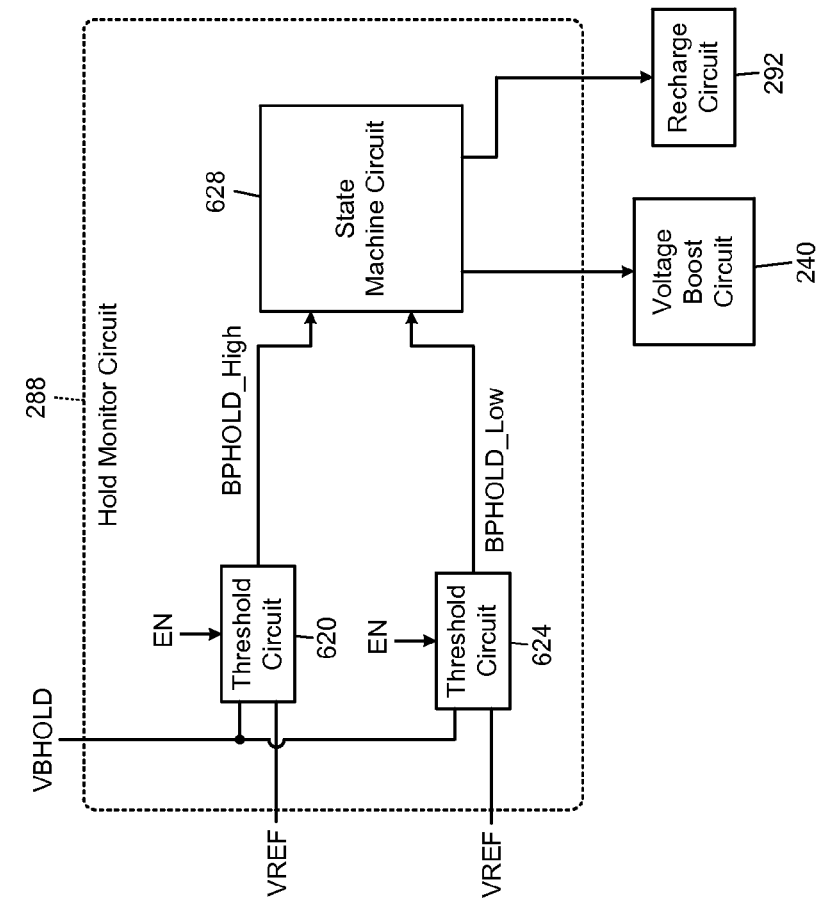
FIGS. 13A-13B are block diagrams of example implementations of a hold monitor circuit.
Figure 13A:
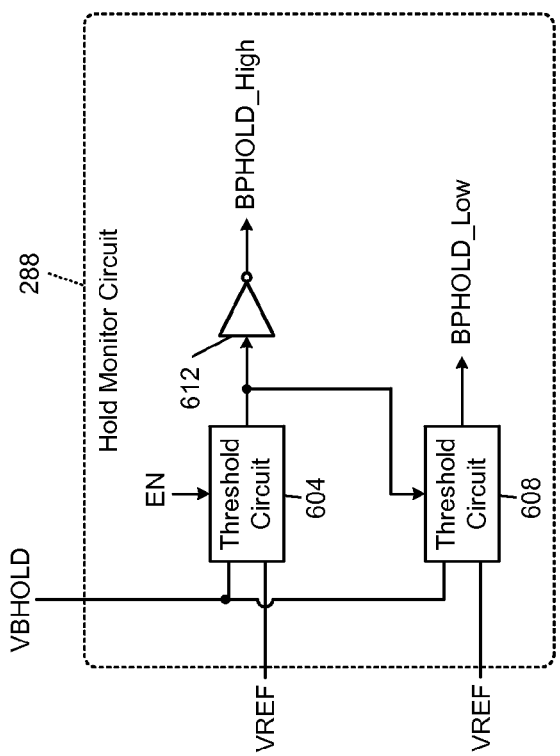

Referring now to FIG. 13A, an example implementation of the hold monitor circuit 288 is shown. A threshold circuit 604 compares the voltage of BPHOLD, VBPHOLD, to a reference voltage while an enable signal is present. The output of the threshold circuit 604 serves as the enable signal for a threshold circuit 608 and is input to an inverter 612. An output of the inverter 612 is a BPHOLD_High signal indicating that recharging of the BPHOLD from the voltage boost circuit 240 can stop. For example only, the threshold circuit 604 may compare VBPHOLD to a range between 2.4 V and 2.8 V.

The threshold circuit 608 compares VBPHOLD to a threshold voltage and outputs a BPHOLD_Low signal in response. The BPHOLD_Low signal indicates when the voltage of BPHOLD has dropped too low and recharging is necessary. For example only, the threshold circuit 608 compares VBPHOLD to a voltage in the range of 2.2 V to 2.4 V.

Referring now to FIG. 13B, another example implementation of the hold monitor circuit 288 is shown. A threshold circuit 620 generates a BPHOLD_High signal when VBPHOLD is greater than a reference voltage. A threshold circuit 624 generates a BPHOLD_Low signal when VBPHOLD decreases below another reference voltage. A state machine circuit 628 controls the voltage boost circuit 240 and/or the recharge circuit 292 in response to the BPHOLD_High signal and the BPHOLD_Low signal, as described in more detail below.

In a significantly simplified system, the state machine circuit 628 could be implemented as an SR latch, which receives the BPHOLD_Low signal at a set input and receives the BPHOLD_High at a reset input. An output Q of the latch would be provided to the recharge circuit 292 and the voltage boost circuit 240. Therefore, when the BPHOLD_Low signal is generated, the latch 628 outputs an enable signal to enable the voltage boost circuit 240 and the recharge circuit 292. This charges up BPHOLD using the boosted voltage. Once the BPHOLD_High signal is generated, resetting the latch 628, the output Q of the latch 628 disables the recharge circuit 292 and the voltage boost circuit 240, ending the recharging.

Figure 14:
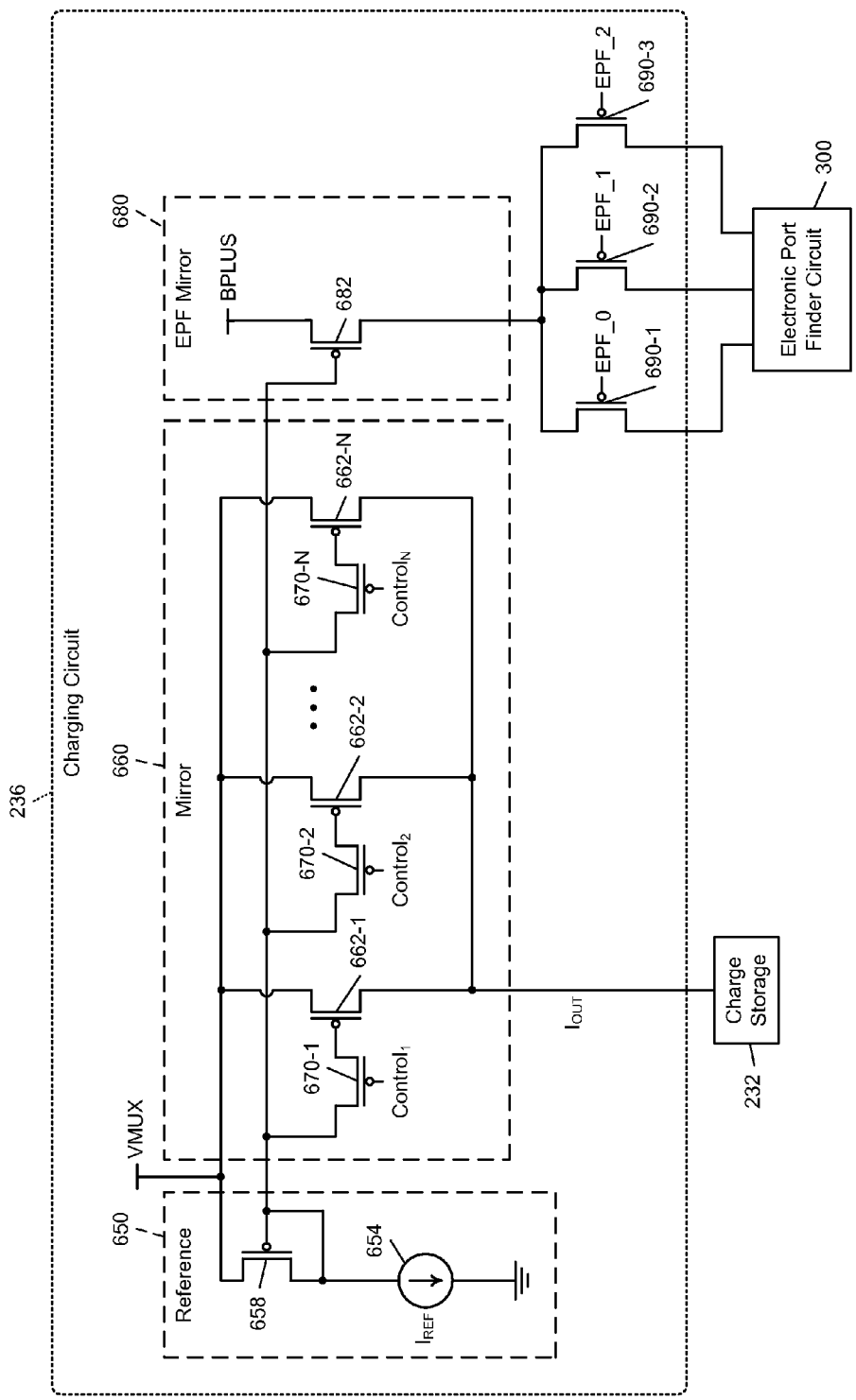
FIG. 14 is a schematic of an example implementation of a charging circuit.

Referring now to FIG. 14, an example implementation of the charging circuit 236 is shown. A reference block 650 generates a reference current $I_{REF}$ 654 through a transistor 658. Additionally, or alternatively, the transistor 658 may be cascoded with one or more additional transistors to improve power supply rejection. In various implementations, $I_{REF}$ 654 may be generated using a resistor. Alternatively, a temperature-compensated or temperature-independent current generator may be used. However, the temperature within the patient may vary within a small range, making a resistor an acceptable current generator.

The reference current through the transistor 658 is mirrored in a mirror block 660 through N current mirror transistors 662-1, 662-2, . . . 662-N (collectively, current mirror transistors 662). The control terminals of each of the current mirror transistors 662 may be selectively connected to the control terminal of the transistor 658 via pass transistors 670-1, 670-2, . . . 670-N (collectively, pass transistors 670). The pass transistors 670 are respectively controlled by control lines $Control_1$, $Control_2$, . . . $Control_N$ (collectively, control lines). The aggregated current from the current mirror transistors 662 is referred to as $I_{OUT}$, and the values of the control lines therefore control how large $I_{OUT}$ is. The mirror block 660 provides $I_{OUT}$ to the capacitor 232.

In various implementations, the current mirror transistors 662 may be sized in a binary fashion to allow for a high dynamic range of control. The $I_{OUT}$ generated by the mirror block 660 may vary, for example, from 0.5 milliamps to 5.75 milliamps. The number of transistors current mirror transistors 662 may be one or may be any integer greater than one. When there is only one current mirror transistor 662, the level of $I_{OUT}$ may be regulated using a different mechanism, such as by adjusting $I_{REF}$ 654.

For operating the electronic port finder circuit 300, an electronic port finder mirror 680 may be included. The electronic port finder mirror 680 may include a transistor 682 whose control terminal is connected to the control terminal of the transistor 658. In practical implementations, additional current mirror legs may be present, and the current reference may be transferred to the transistor 682 via additional mirror transistors, such as NMOS mirror transistors.

In various implementations, the charging circuit 236 may include a plurality of transistors 690 to selectively provide current to different transmit coils of the electronic port finder circuit 300 from the electronic port finder mirror 680. For example, transistors 690-1, 690-2, and 690-3 may be controlled in a mutually exclusive fashion to provide current to respective coils of the electronic port finder circuit 300.

In various implementations, the electronic port finder circuit 300 may be operated at only BPLUS, not at VMUX from the multiplexer circuit 244, which will be either BPLUS or BATT2X. Because BPLUS is a lower voltage, the components of the electronic port finder mirror 680 may be connected directly to BPLUS instead of VMUX. The components, such as the transistor 682, may be implemented as devices having lower maximum voltage limits, which may allow the components to be smaller in size or exhibit other advantages. In various implementations, charging the capacitor 232 may be mutually exclusive to operating the electronic port finder circuit 300.

Figure 15:
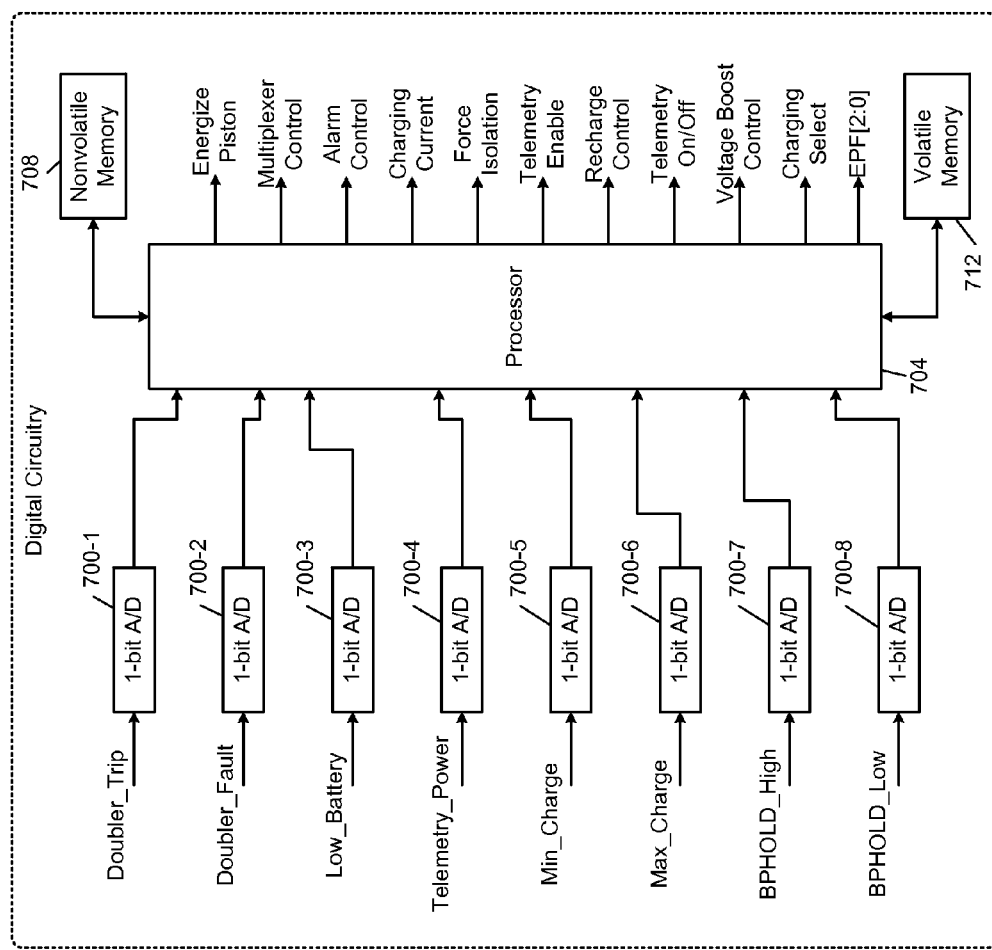
FIG. 15 is a block diagram of example digital circuitry.

Referring now to FIG. 15, an example functional block diagram of the digital circuitry 248 is presented. The digital circuitry 248 is shown in FIG. 15 including analog-to-digital converters 700 even though such converters are not strictly digital. The analog-to-digital converters 700 include a converter 700-1 that receives the Doubler_Trip signal, a converter 700-2 that receives the Doubler_Fault signal, a converter 700-3 that receives the Low_Battery signal, a converter 700-4 that receives the Telemetry_Power signal, a converter 700-5 that receives the Min_Charge signal, a converter 700-6 that receives the Max_Charge signal, a converter 700-7 that receives the BPHOLD_High signal, and a converter 700-8 that receives the BPHOLD_Low signal.

The digital values are received by a processor 704, which operates using nonvolatile memory 708, which may include firmware, and volatile memory 712, which may include temporary storage. For example only, the nonvolatile memory 708 may include flash memory and/or read-only memory, while the volatile memory 712 may include random access memory. The processor 704 generates various outputs to control other elements of the implantable infusion device 200. In various implementations, the processor 704 may be supplemented by custom or programmable logic that performs functions otherwise described as being performed by the processor 704. Various inputs and various outputs of the processor 704 may therefore be received/outputted by the custom or programmable logic.

Figure 16:
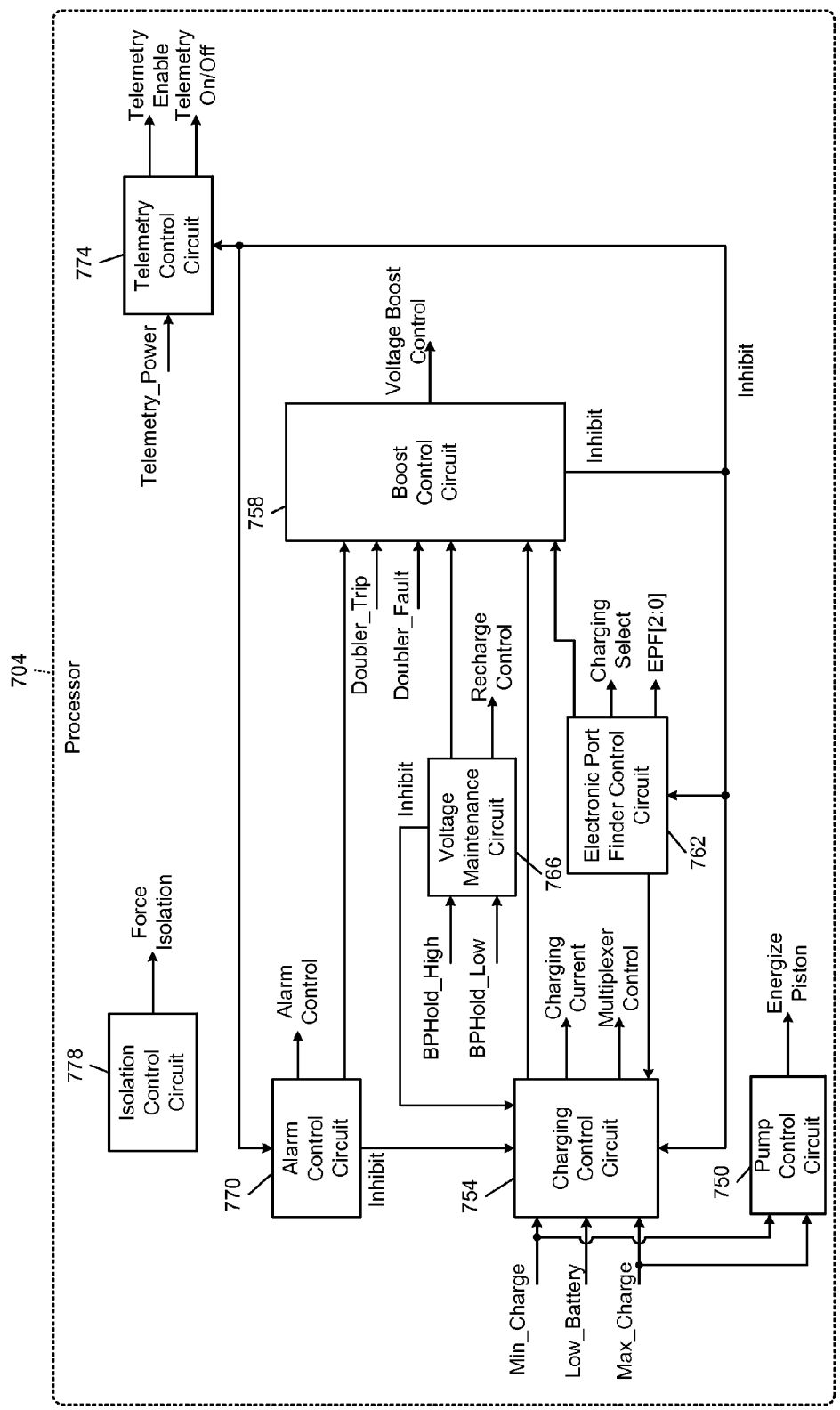
FIG. 16 is a functional block diagram of example functions of a processor.

Referring now to FIG. 16, a simplified functional block diagram of an example implementation of the processor 704 is shown. Although the processor 704 is shown in FIG. 16 to include the following circuits, these circuits may be implemented as discrete circuitry either inside or outside of a processor, such as in a system-on-chip or application specific integrated circuit. Further, in accordance with the definition of circuits set out below, these circuits are not necessarily each separate, mutually exclusive, hardware elements. In various implementations, code executed by the processor 704 may be replaced by digital state machines implemented in custom logic or programmable logic.

A pump control circuit 750 determines when the pump 212 should be actuated and instructs a charging control circuit 754 to store up enough charge to actuate the pump 212. In various implementations, the pump control circuit 750 receives the Min_Charge signal when enough charge is present, as evidenced by a capacitor voltage reaching a predetermined threshold. Once enough charge is present and a pump stroke is desired, the pump control circuit 750 outputs a signal to the pump actuator circuit 228 to energize the solenoid coil 224. The pump control circuit 750 may additionally or alternatively operate in response to the Max_Charge signal.

The charging control circuit 754 also receives the Min_Charge signal, which indicates that charging of the capacitor 232 can be stopped. The charging control circuit 754 also receives the Low_Battery signal, which indicates that charging should be slowed, paused, or stopped, as described in more detail below. The charging control circuit 754 also receives the Max_Charge signal, which indicates that a boosted voltage is necessary to effectively continue charging the charge storage 232. The charging control circuit 754 then instructs a boost control circuit 758 to turn on the voltage boost circuit 240 to provide the additional voltage coverage needed. The charging control circuit 754 also provides multiplexer control to the multiplexer circuit 244 to select the boosted voltage from the voltage boost circuit 240.

The charging control circuit 754 controls the amount of charging current generated by the charging circuit 236. This charging current may be partially reduced or decreased to zero in response to the Low_Battery signal.

An electronic port finder control circuit 762 controls the charging circuit 236 to output current to the electronic port finder circuit 300 and includes three signals EPF2, EPF1, and EPF0 to select which of the coils will be energized. The electronic port finder control circuit 762 also disables the charging control circuit 754 and the boost control circuit 758 while electronic port finding is being performed.

A voltage maintenance circuit 766 receives the BPHOLD_High and BPHOLD_Low signals. In response to these signals, the voltage maintenance circuit selectively enables the boost control circuit 758 and provides a recharge control signal to the recharge circuit 292 of FIG. 2. While the BPHOLD bus is recharging, the voltage maintenance circuit 766 may inhibit the charging control circuit 754.

An alarm control circuit 770 determines when an alarm should be sounded and, in response, instructs the boost control circuit 758 to enable the voltage boost circuit 240 of FIG. 2. At the same time, the alarm control circuit 770 inhibits the charging control circuit 754. Once startup of the voltage boost circuit 240 is complete, the alarm control circuit 770 instructs the alarm circuit 252 to generate the alarm sound.

A telemetry control circuit 774 receives the Telemetry_Power signal and, in response to the Telemetry_Power signal, turns off telemetry. Once the Telemetry_Power signal is no longer present, the telemetry control circuit 774 recognizes that the battery voltage BPLUS has recovered and telemetry can be turned back on. The telemetry control circuit 774 can also temporarily disable telemetry, such as based on an inhibit request from the boost control circuit 758.

The boost control circuit 758 controls the voltage boost circuit 240 of FIG. 2 based on a boost request from the alarm control circuit 770, the voltage maintenance circuit 776, or the charging control circuit 754. The boost control circuit 758 also can initiate boost based on the Doubler_Trip signal and/or the Doubler_Fault signal.

When the voltage boost circuit 240 is started, a larger in-rush current may occur before a lower steady-state current is established. During this in-rush time, the boost control circuit 758 may inhibit the alarm control circuit 770 from activating the alarm, may inhibit telemetry via the telemetry control circuit 774, may inhibit electronic port finding via the electronic port finder control circuit 762, and may inhibit charging via the charging control circuit 754.

An isolation control circuit 778 selectively outputs a force isolation signal to the comparison circuit 280 of FIG. 2, which causes the isolation circuit 276 of FIG. 2 to isolate BPHOLD from BPLUS. This may be done for testing purposes.

Figure 17:
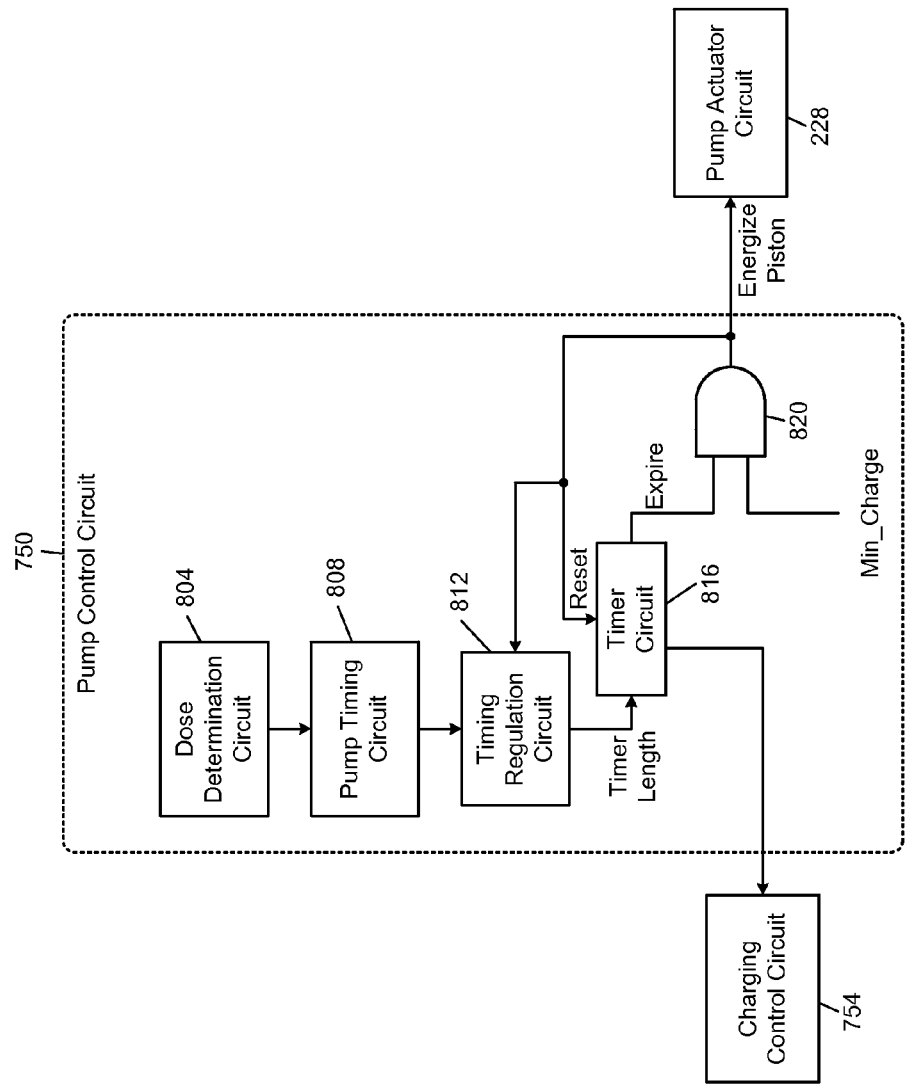
FIG. 17 is a functional block diagram of an example implementation of a pump control circuit.

Referring now to FIG. 17, a simplified functional block diagram of an example implementation of the pump control circuit 750 is presented. A dose determination circuit 804 determines how much drug per unit of time will be delivered to the patient. This may be based on values provided by a clinician and/or by the patient themself. This value may remain relatively constant throughout the day, but may be interrupted by one or more boluses which may be higher doses of drug provided at certain times of the day. In addition, boluses may be delivered at certain times during a week or a month and/or may be delivered while the patient is in a clinical setting.

The dose determination circuit 804 may have a number of special operating modes, such as a post-manufacturing mode, in which sterile solution stored in the reservoir 216 during manufacturing is very slowly pumped out to keep all of the parts of the implantable infusion device 200 operating correctly while the implantable infusion device 200 is shipped, stored, and sold. In addition, the dose determination circuit 804 may have a mode in which a very high dosage rate is produced to prime the catheter, such as during the operation to implant the implantable infusion device 200 in a patient.

Based on the determined dose from the dose determination circuit 804, a pump timing circuit 808 determines an average time between piston strokes of the pump in order to achieve the desired dosage. The timing regulation circuit 812 controls the pump actuator circuit 228 of FIG. 2 and the charging control circuit 754 of FIG. 16 to achieve the average timing specified by the pump timing circuit 808. For various reasons, such as a low battery voltage or other higher-priority current demands, charging the capacitor 232 may take longer than the desired average time. The timing regulation circuit 812 takes this into account and therefore reduces the amount of time for the next piston stroke to attempt to deliver the appropriate amount of drug per unit of time.

The timing regulation circuit 812 provides a timer length value to a timer circuit 816, specifying the desired time until the next pump stroke. The timer circuit 816 counts down (or up, depending on the implementation), and before the timer is going to expire, the timer circuit 816 instructs the charging control circuit 754 to begin charging the capacitor 232. The timer circuit 816 may learn over time how long this charging process takes and actuate the charging control circuit 754 at the appropriate time before expiration of the timer. The timer circuit 816 may take into account other current loads, such as telemetry, when determining how soon charging needs to begin.

When the timer expires, the timer circuit 816 provides an expire signal to an AND gate 820. The AND gate 820 outputs an energize piston signal to the pump actuator circuit 228 when both the expire signal is received and the Min_Charge signal is present. For example only, the pump actuator circuit 228 may include one or more transistors arranged in parallel that rapidly discharge the charge storage 232 into the solenoid coil 224 of the pump 212 in order to actuate the piston and pump the drug through the catheter 220 and into the patient.

Figure 18:
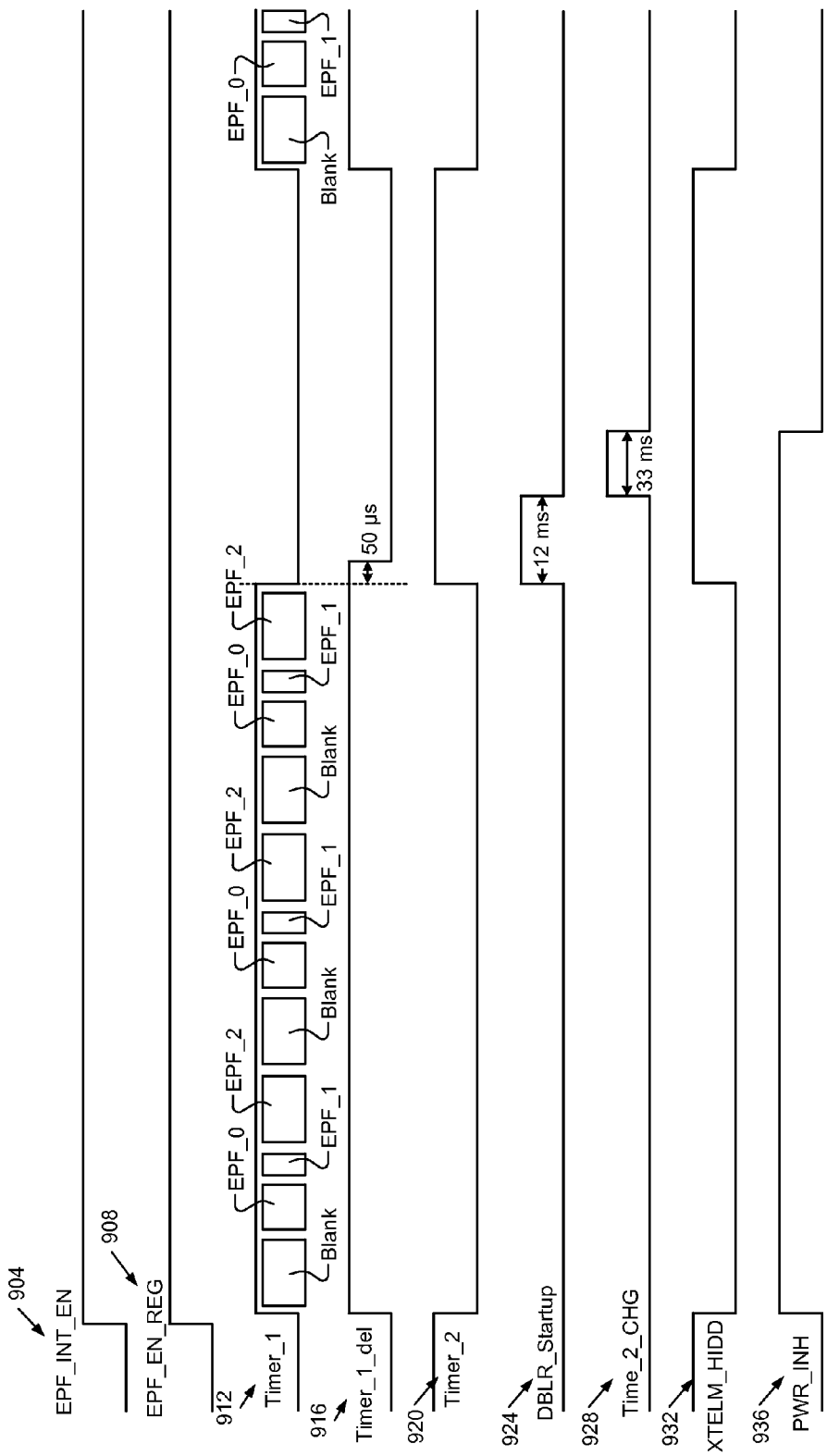
FIG. 18 shows example traces of control signals that allow for electronic port finder interleaving.

Referring now to FIG. 18, a plot of various control signals over time is presented. Traces include an electronic port finder enable signal 904, an electronic port finder enable register 908, a first timer 912, a delayed first timer 916, a second timer 920, a Doubler_Startup signal 924, a time to charge signal 928 for the BPHOLD rail, an XTELM_HIDD signal 932, and a PWR_INH signal 936.

The signals 904 and 908 are active high to enable electronic port finder operation. The signal 912 is active high to delineate when electronic port finding is operated. While the signal 912 is high, interleaving of the electronic port finder coils is shown, with a blank interval followed by coil 0, followed by coil 1, and followed by coil 2. This pattern repeats while timer_1 remains asserted. Alternatively, the pattern could have the electronic port finder coils energized in a different order, and the blank period could be at a different location, such as after each time the three electronic port finder coils were energized instead of before. Additional information on interleaving coils, the gaps between the coils, and the blank periods can be found in commonly assigned application Ser. No. 13/045,683, filed Mar. 11, 2011, the disclosure of which is hereby incorporated by reference in its entirety.

The delayed timer signal 916 is not de-asserted until a predetermined period of time after the signal 912 is de-asserted. This is used to inhibit telemetry so that there is no interference between electronic port finding and telemetry. The predetermined period may, for example, be 50 microseconds.

The signal 920 is inverted compared to the signal 912 and is active high to indicate that other functions can be performed now that electronic port finding operation has paused. The signal 924 indicates that the voltage boost circuit 240 of FIG. 2 is starting up, a period during which various functionality, including telemetry, is inhibited. In this example, startup is shown to take 12 milliseconds.

The reason for the doubler starting up is shown in signal 928, which depicts the amount of time necessary to charge the BPHOLD bus from the boosted voltage created by the voltage boost circuit 240. This indicates that the voltage of BPHOLD had decreased too far and needed to be boosted. For example only, the charging time may be 33 milliseconds. This may be a fixed number or may be a measurement of the actual charging time. The signal 932 enables telemetry and may disable telemetry whenever signal 912 is high. The signal 936 exerts an additional inhibit on telemetry, which lasts until after BPHOLD is charged up (at the end of the 33 millisecond window of signal 928).

Figure 19:
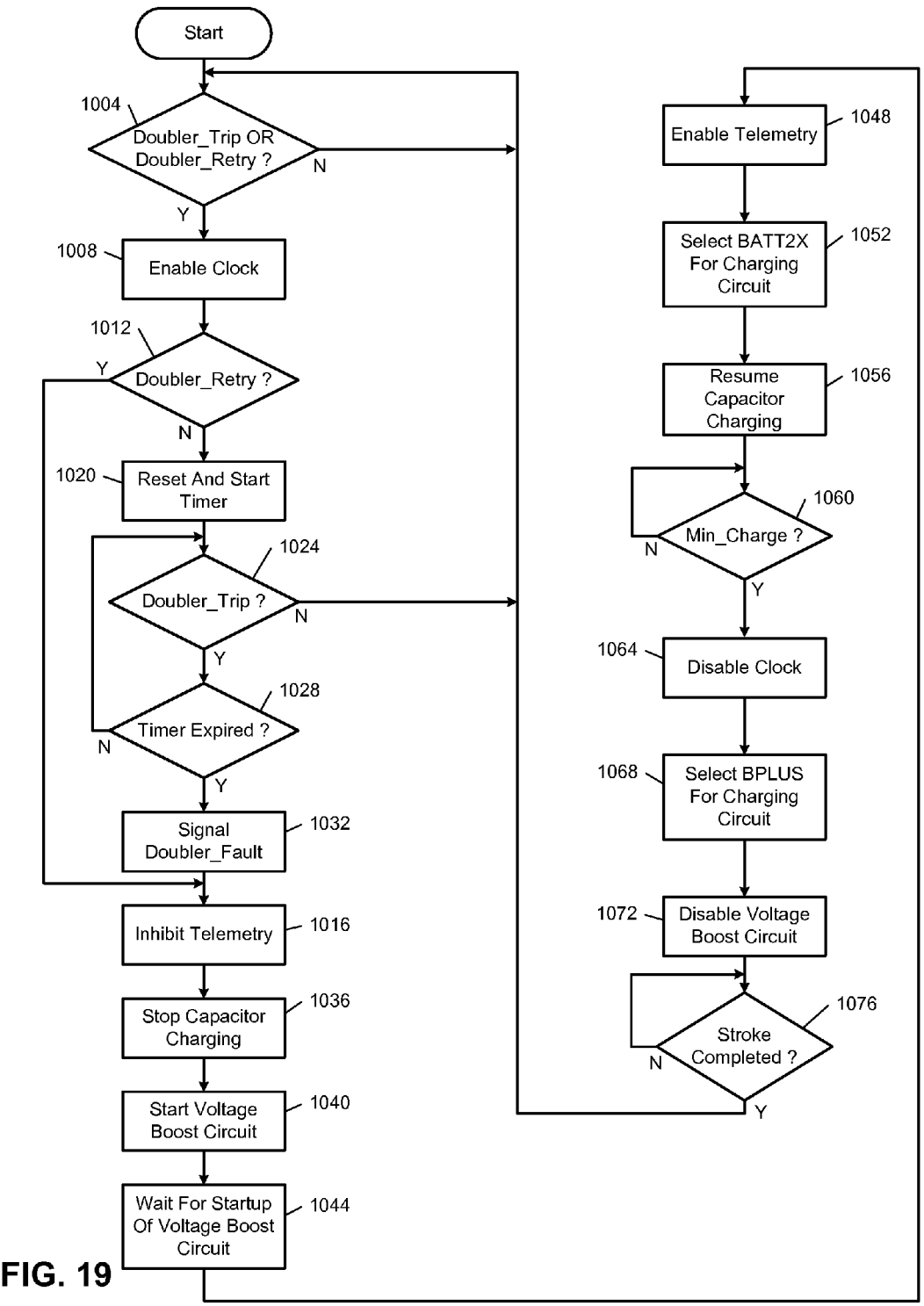
FIG. 19 is a flowchart depicting example operation of voltage boost control.

Referring now to FIG. 19, a flowchart depicts example operation of the boost control circuit 758 of FIG. 16. Control begin at 1004, where control determines whether a Doubler_Trip signal or a Doubler_Retry signal is present. If so, control continues at 1008; otherwise, control returns to 1004. At 1008, control enables a clock for use by the voltage boost circuit 240 of FIG. 2. For example only, the clock may run at 100 KHz.

Control continues at 1012, where control determines whether the Doubler_Retry signal is present. If so, control transfers to 1016; otherwise, control continues at 1020, where control resets and starts a timer. The timer is for a predetermined period of time that eliminates glitches in the Doubler_Trip signal, such as twenty milliseconds. Control continues at 1024, where control determines whether the Doubler_Trip signal is still present. If so, control transfer to 1028; otherwise, control returns to 1004.

At 1028, control determines whether the timer has expired. If so, control continues at 1032; otherwise, control returns to 1024. At 1032, control signals a Doubler_Fault and continues at 1016. At 1016, control inhibits telemetry and continues at 1036, where capacitor charging is also stopped. Control continues at 1040, where the voltage boost circuit is started and continues at 1044, where control waits for startup of the voltage boost circuit to complete. Control continues at 1048, where telemetry is re-enabled, and continues at 1052, where BATT2X is selected by the multiplexer circuit 244 of FIG. 2 for charging.

Control continues at 1056, where capacitor charging is resumed. Throughout FIG. 19, while the capacitor is being charged, a Low_Battery event may delay or stop the capacitor charging. For example only, a capacitor charging back-off process, such as is described in FIG. 23 below, may be implemented.

Control continues at 1060, where control determines whether the Min_Charge signal is present. If so, control continues at 1064; otherwise, control remains in 1060. At 1064, control disables the clock, and at 1068, control selects BPLUS for the charging circuit 236 using the multiplexer circuit 244. Control continues at 1072, where the voltage boost circuit is disabled, and control continues at 1076. Control remains at 1076 until the pump stroke is completed, and then control returns to 1004. In various implementations, the pump stroke may sometimes be significantly delayed after the Min_Charge signal is present. If so, the voltage on the capacitor may decrease over that delay, and therefore control may return to 1016 to restart the voltage boost circuit and recharge the capacitor up to the required level.

Figure 20:
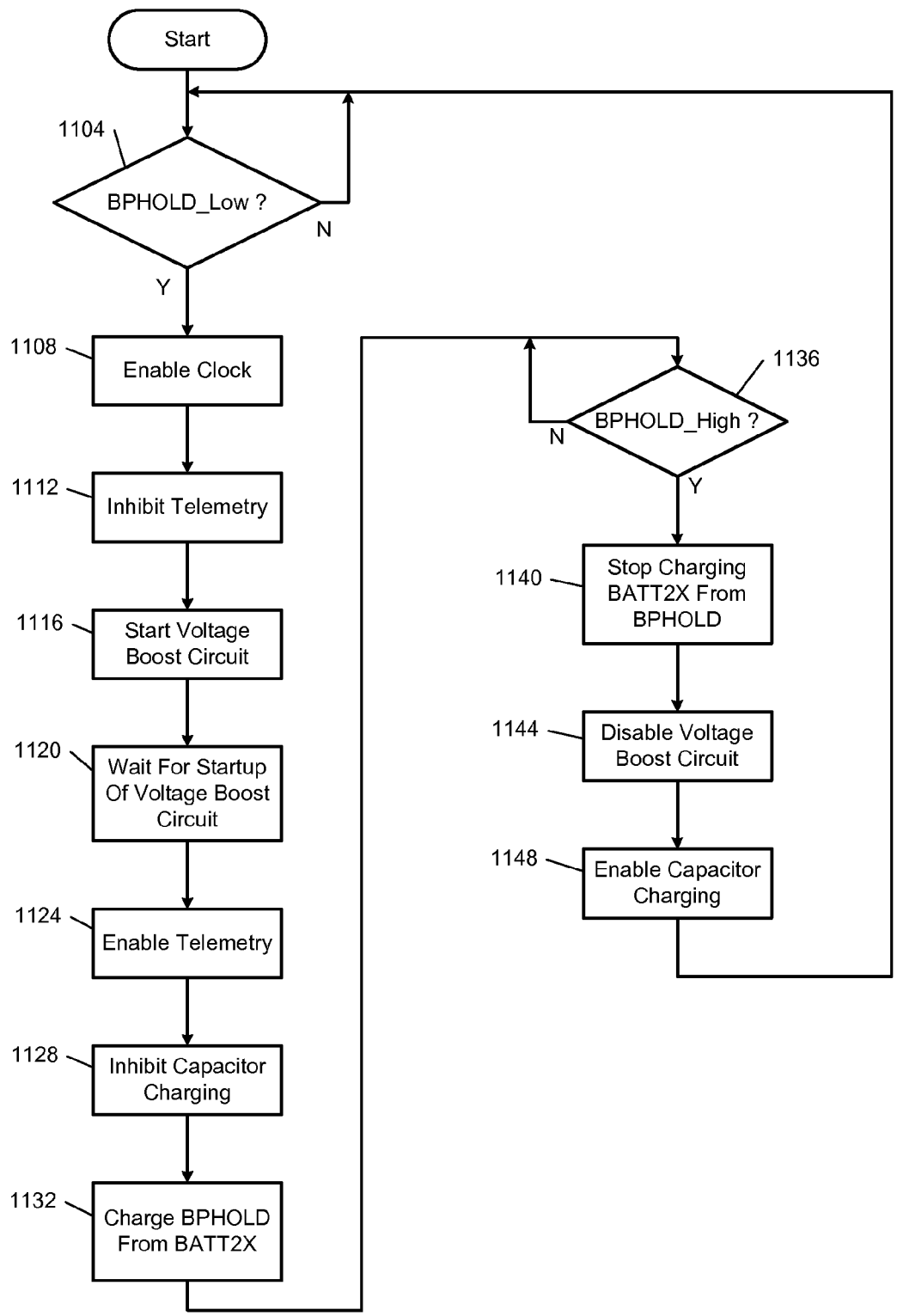
FIG. 20 is a flowchart depicting example operation of voltage maintenance for a node.

Referring now to FIG. 20, a flowchart depicts example operation of the voltage maintenance circuit 766 of FIG. 16. Control begins at 1104, where control determines whether the BPHOLD_Low signal is present. If so, control transfers to 1108; otherwise, control returns to 1104. At 1108, control enables a clock for the voltage boost circuit. Control continues at 1112, where telemetry is inhibited. For example only, telemetry may be inhibited by making a telemetry inhibit request, which is granted once an ongoing telemetry operation completes.

Control continues at 1116, where the voltage boost circuit is started. Control continues at 1120 where control waits for startup of the voltage boost circuit to complete. Control continues at 1124, where telemetry is enabled, and continues at 1128, where capacitor charging is inhibited. Control continues at 1132, where BPHOLD is charged from BATT2X. Control continues at 1136, where control determines whether the BPHOLD_High signal is present. If so, control continues at 1140; otherwise, control remains at 1136. At 1140, control stops charging BPHOLD from BATT2X and control continues at 1144. At 1144, control disables the voltage boost circuit. Control continues at 1148, where capacitor charging is re-enabled and control continues to 1104.

Figure 21:
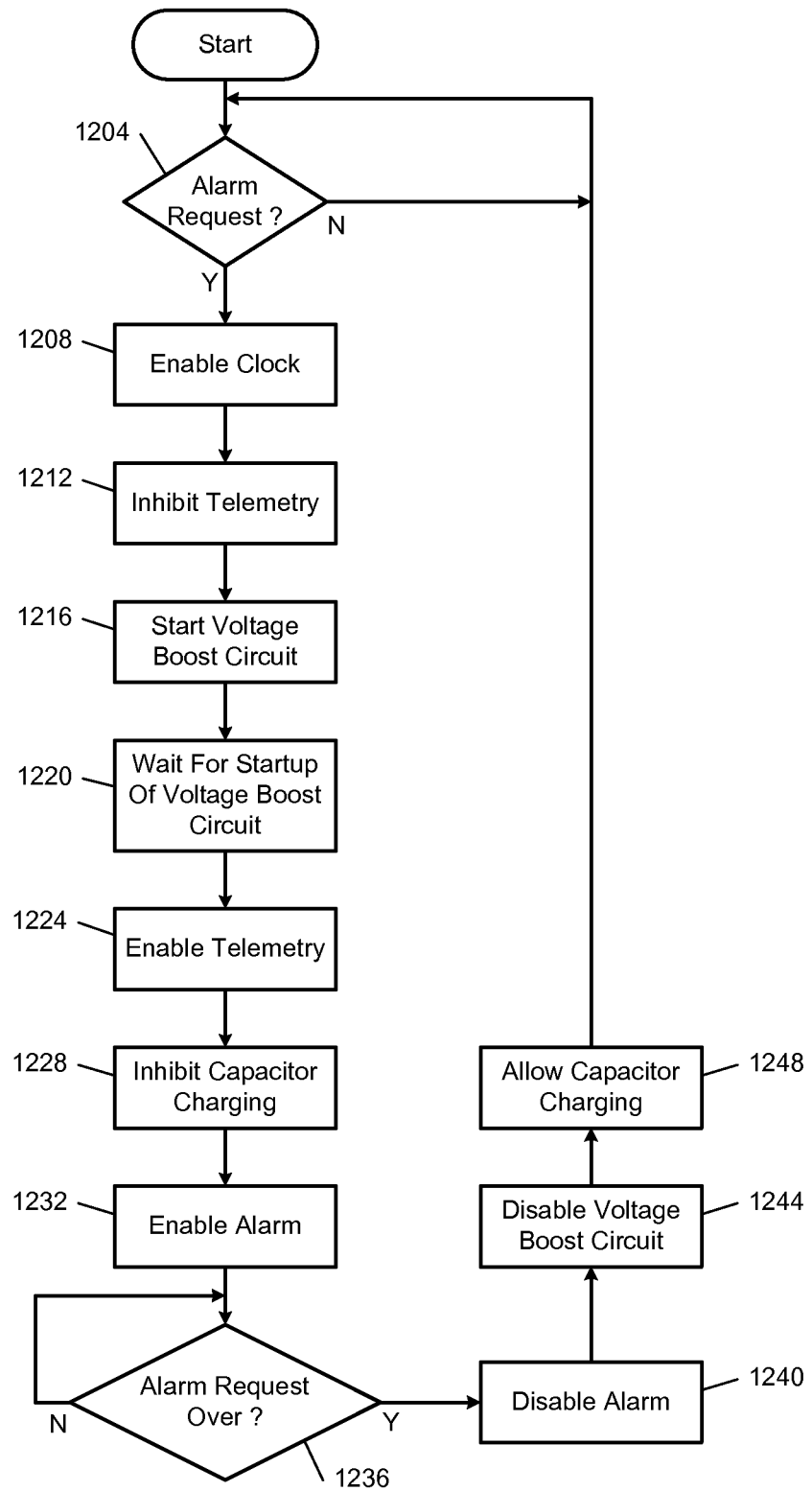
FIG. 21 is a flowchart depicting example operation of an alarm circuit.

Referring now to FIG. 21, example operation of the alarm control circuit 770 of FIG. 16 is presented. Control begins at 1204, where control determines whether an alarm request is present. If so, control continues at 1208; otherwise, control remains at 1204. At 1208, control enables a clock for operating the voltage boost circuit 240 of FIG. 2. Control continues at 1212, where telemetry is inhibited, and continues at 1216, where the voltage boost circuit is started. Control continues at 1220, where control waits for startup of the voltage boost circuit to be completed. Control continues at 1224, where telemetry is enabled, and continues at 1228, where capacitor charging is inhibited. Control continues at 1232, where the alarm is sounded. Control continues at 1236, where control determines whether the request for an alarm is over. If so, control transfers to 1240; otherwise, control remains at 1236. At 1240, control disables the alarm and continues at 1244, where the voltage boost circuit is disabled. Control continues at 1248, where capacitor charging is enabled, and returns to 1204.

Figure 22A:
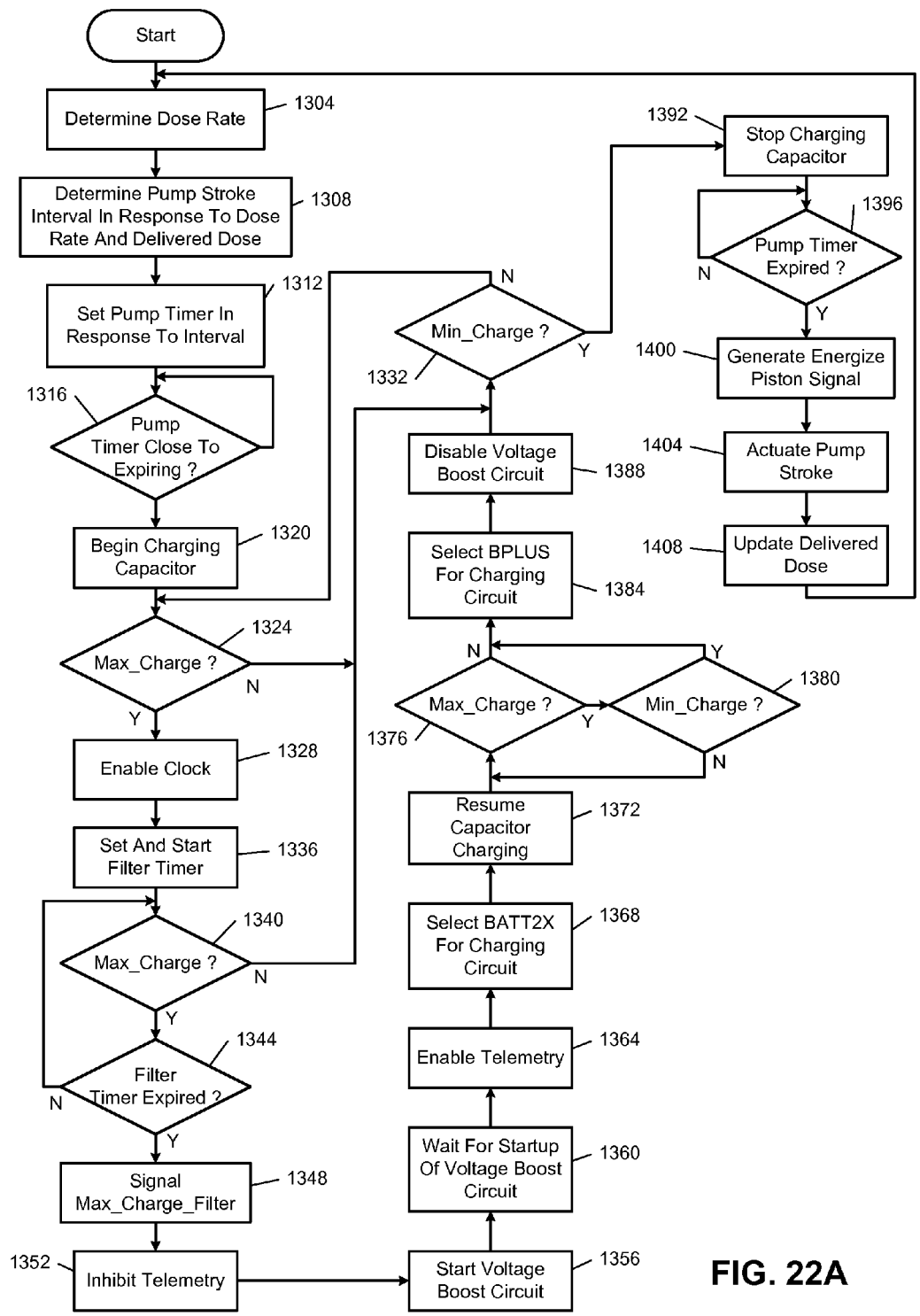
FIG. 22A is a flowchart depicting example operation of capacitor charging.

Referring now to FIG. 22, a flowchart depicts example charging control performed by the pump control circuit 750 and the charging control circuit 754 of FIG. 16. Control begins at 1304, where a desired dose rate is determined. Control continues at 1308, where a desired pump stroke interval is determined in response to the dose rate of 1304 as well as recorded information concerning the doses delivered so far.

Control continues at 1312, where a pump timer is set in response to the interval of 1308. Control continues at 1316, where control determines whether the pump timer is close to expiring. If so, control transfers to 1320; otherwise, control remains at 1316. At 1320, control begins charging the capacitor 232. Control continues at 1324, where if the Max_Charge signal is present, control transfers to 1328; otherwise, control transfers to 1332.

At 1328, control enables the clock for the voltage boost circuit 240 of FIG. 2. Control continues at 1336, where control sets and starts a filter timer. Control continues at 1340, where if the Max_Charge signal is still present, control continues at 1344; otherwise, control transfers to 1332. At 1344, control determines whether the filter timer has expired. If so, control transfers to 1348; otherwise, control returns to 1340. At 1348, control signals Max_Charge_Filter and continues at 1352, where telemetry is inhibited. Control continues at 1356, where the voltage boost circuit is started. Control continues at 1360, where control waits for the startup to finish.

Control then continues at 1364, where telemetry is enabled, and continues at 1368, where BATT2X is selected for charging the charge storage 232. Control then resumes charging the capacitor 232 at 1372. Control continues at 1376, where if the Max_Charge signal is still present, control transfers to 1380; otherwise, control continues at 1384. At 1380, control determines whether the Min_Charge signal is present and, if so, control transfers to 1384; otherwise, control returns to 1376. At 1384, control selects BPLUS for charging the capacitor 232 and continues at 1388, where the voltage boost circuit is disabled.

Control continues at 1332, where if the Min_Charge signal is present, control transfers to 1392; otherwise, control returns to 1324. At 1392, control stops charging the capacitor 232 and continues at 1396. At 1396, control determines whether the pump timer has expired. If so, control transfers to 1400; otherwise, control remains at 1396. At 1400, control sends an energized signal to the pump actuator circuit 228 of FIG. 2. Control continues at 1404, where the pump actuator circuit 228 energizes the solenoid coil and causes a stroke of the pump. As the pump solenoid is energized, the inductance of the solenoid stores electrical energy. In various implementations, some of this energy is recovered after the piston is actuated, with the recovered energy being stored back on the capacitor. See commonly assigned U.S. Pat. No. 7,927,326 to Sarkinen et al., issued Apr. 19, 2011, the disclosure of which is hereby incorporated by reference in its entirety. Control continues at 1408, where control updates delivered dose information to reflect the drug delivered at 1404. Control then returns to 1304.

Figure 22B:
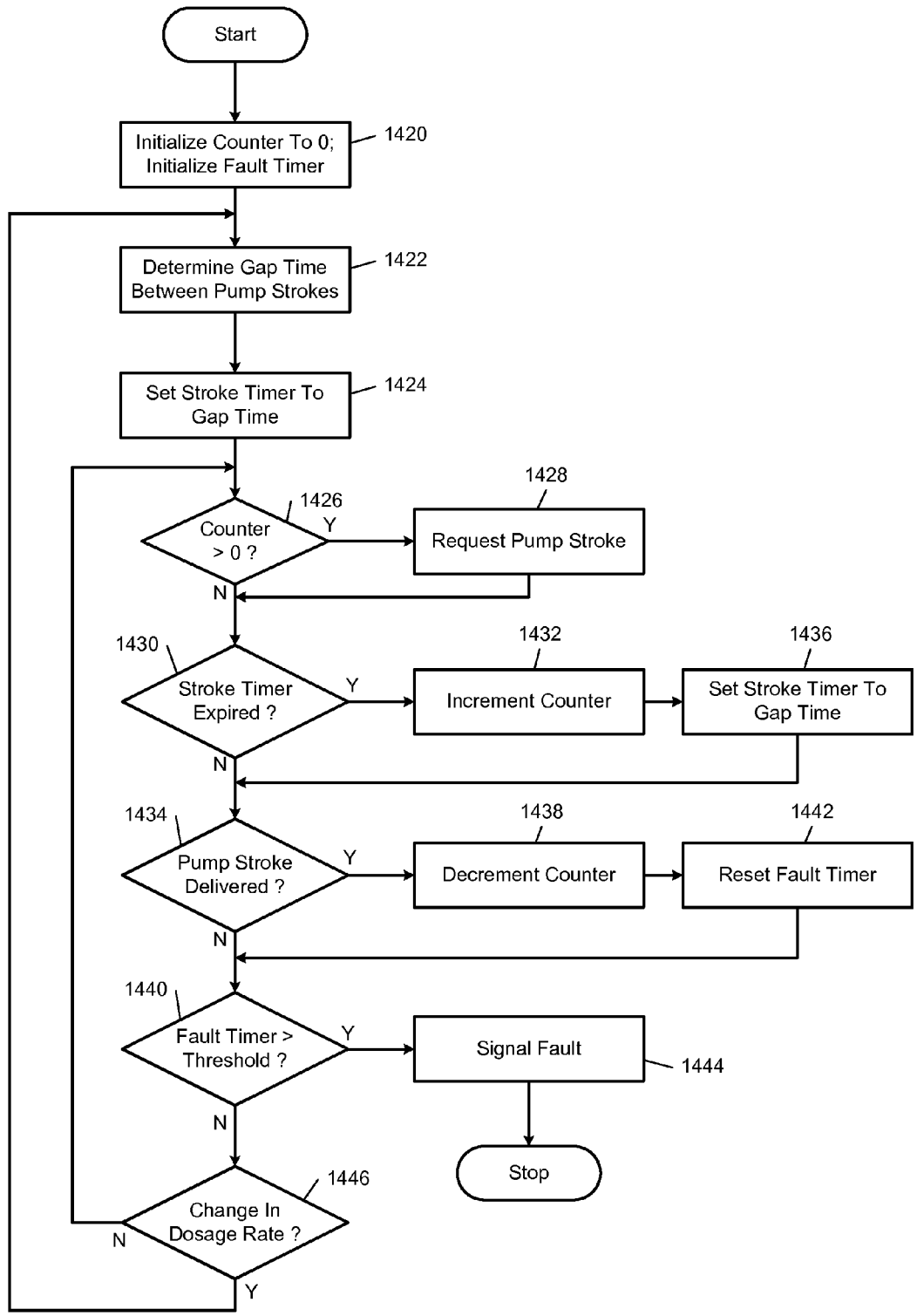
FIG. 22B is a flowchart depicting example operation of pump stroke monitoring.

Referring now to FIG. 22B, a pump stroke catch-up process is shown. This process can be used in conjunction with or alternatively to elements of FIG. 22A, such as 1308, 1312, and 1316. Control begins at 1420 where control initializes a counter to 0 and initializes a fault timer. For example, the fault timer may be initialized to zero and may then begin increasing. Control continues at 1422, where control determines a gap time between pump strokes based on the dosage rate. For example, the dosage rate may indicate that one pump stroke should be delivered each minute, and therefore the gap time is set to one minute.

Control continues at 1424, where a stroke timer is set to the gap time. The stroke timer then begins decrementing. Once the stroke timer gets to zero, the stroke timer is considered expired, and another stroke will be requested. Control continues at 1426, where control checks whether the counter is greater than zero. If so, control transfer to 1428; otherwise, control transfers to 1430.

At 1428, control requests a pump stroke and control continues at 1430. In various implementations, control requests a single pump stroke at a time and once that pump stroke has been delivered, the next pump stroke is requested. When the counter is greater than one and multiple pump strokes are desired, the pump strokes may be requested consecutively.

At 1430, control determines whether the stroke timer has expired. If so, control transfers to 1432; otherwise, control transfers to 1434. At 1432, control increments the counter and continues at 1436. At 1436, control sets the stroke timer back to the gap time and continues at 1434. At 1434, control determines whether a pump stroke has been delivered. If so, control transfers to 1438; otherwise, control transfers to 1440.

At 1438, control decrements the counter and continues at 1442. At 1442, control resets the fault timer and continues at 1440. The fault timer may track the amount of time since the last pump stroke was delivered. If this time is too great, this may indicate a failure, either of software or hardware. At 1440, control determines whether the fault timer is greater than a threshold. If so, control transfers to 1444 where a fault is signaled and control stops; otherwise, control transfers to 1446.

The threshold may be a fixed value set to be greater than the maximum amount of time between any two pump strokes. In various implementations, the threshold may be based on the gap time. For example, if the gap time is one minute, the fault timer threshold may be set to three minutes; meanwhile, if the gap time between pump strokes is five minutes, the threshold may be set to seven minutes. Although these examples present an offset of two minutes from the gap time, the offset may instead be a percentage of the gap time. Alternatively, another method of determining the threshold, which may be partially or completely based on the gap time, may be used. At 1446, control determines whether a change in the dosage rate has been requested. If so, control returns to 1422, where a new gap time is determined; otherwise, control returns to 1426.

As shown in FIG. 22B, the first pump stroke after a change in dosage rate is not delivered until the first gap time has expired. However, the present disclosure is not limited, and FIG. 22B can be adapted to deliver the first pump stroke at the beginning of the first gap time, such as by initializing the counter to 1 at 1424.

Figure 23:
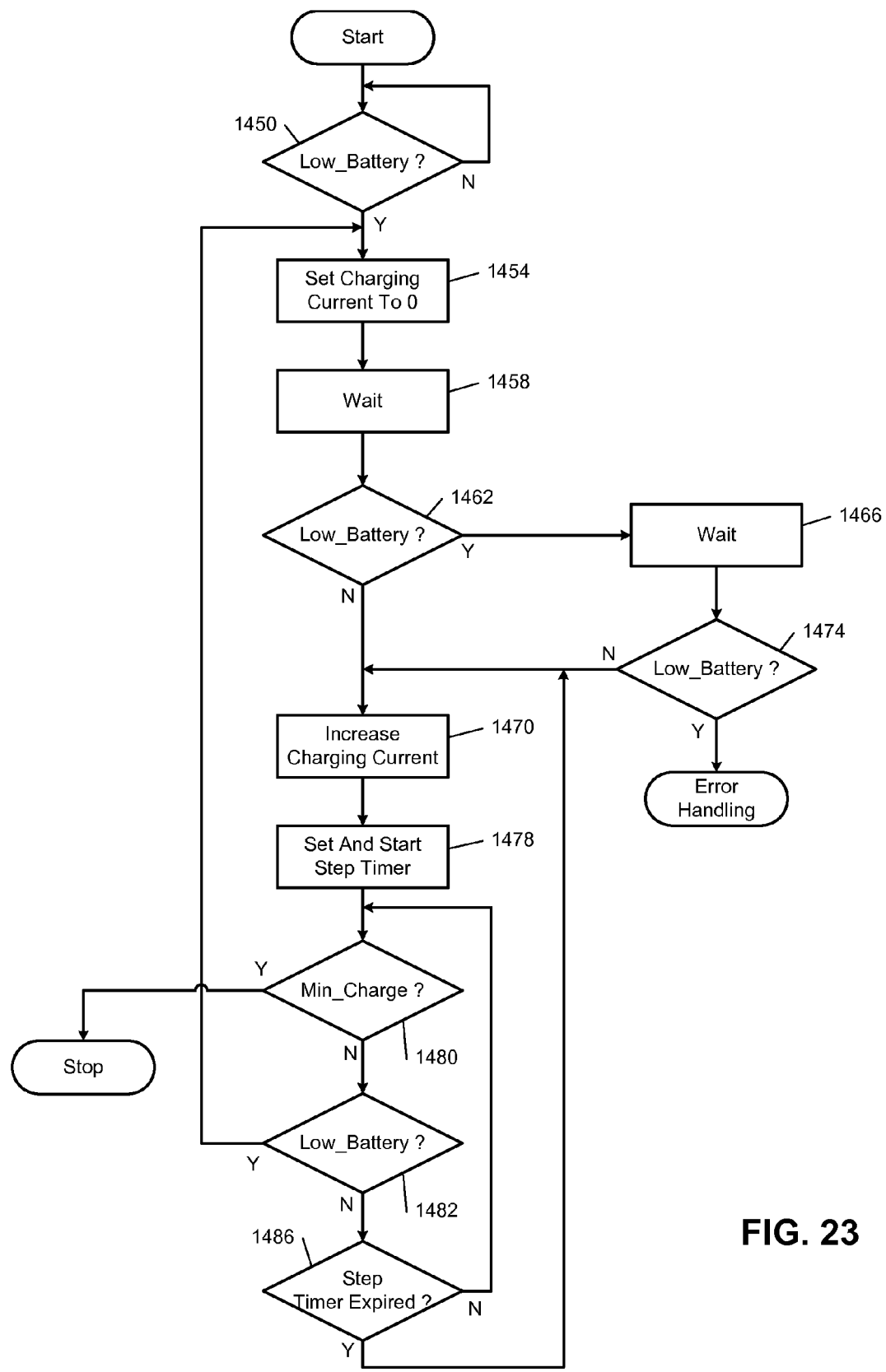
FIG. 23 is a flowchart depicting example operation of a low battery control process.

Referring now to FIG. 23, a flowchart depicts an example response by the charging control circuit 754 of FIG. 16 to the Low_Battery signal. Control begins 1450, where control determines whether the Low_Battery signal is present. If so, control transfers to 1454; otherwise, control remains at 1450. At 1454, control sets the charging current to 0, and continues at 1458. At 1458, control waits for a predetermined period of time to allow the battery voltage to recover. Control continues at 1462, where if the Low_Battery signal is still present, control transfers to 1466; otherwise, control transfers to 1470.

At 1466, control waits for another period of time, which may be longer than the period of 1458. Control then continues at 1474, where if the Low_Battery signal is still present, error handling is performed; otherwise, control transfers to 1470. The error handling may include evaluating whether the implantable infusion device 200 is reaching its end of life.

At 1470, control increases the charging current by an increment. This increment may be a fixed increment, may be a percentage, or may be some predetermined amount based on the previous charging current. Control continues at 1478, where a step timer is set to a value and started. The value of the step timer may be the same for each increasing current or may be different for different increases in current. For example, the step timer value may be greater for each successive increase in current.

Control continues at 1480, where if the Min_Charge signal is present, the capacitor has been charged, and therefore the capacitor charging back-off process of FIG. 23 can stop. Otherwise, control continues at 1482, where if the Low_Battery signal has once again appeared, control returns to 1454; otherwise, control transfers to 1486. If the step timer has expired, control returns to 1470 so that current can once again be increased; otherwise, control returns to 1482.

Figure 24:
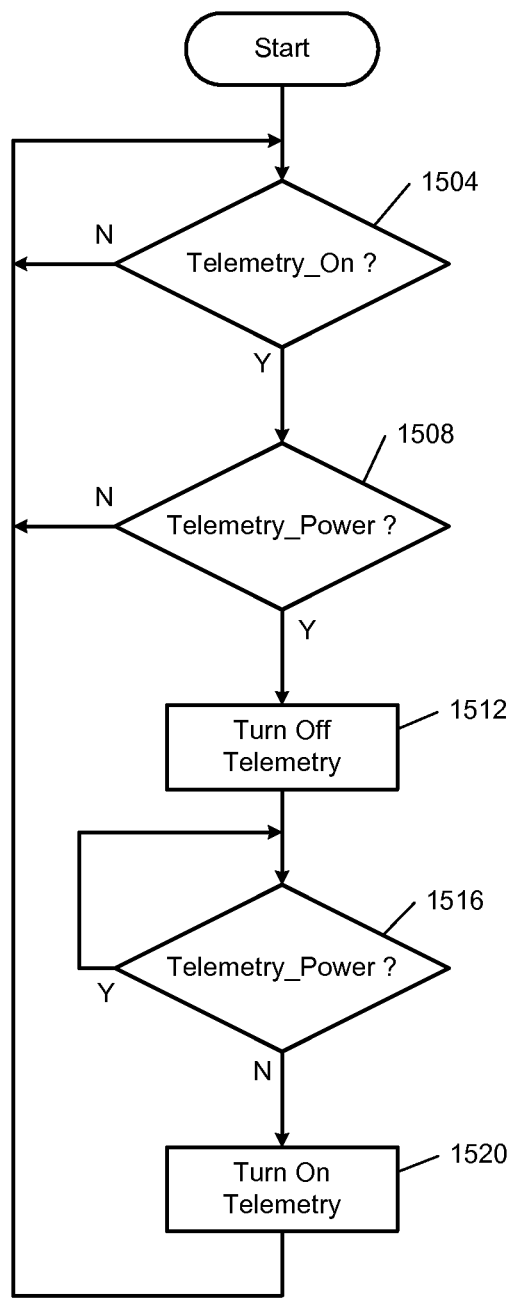
FIG. 24 is a flowchart depicting example control of telemetry circuitry.

Referring now to FIG. 24, a flowchart depicts example operation of the telemetry control circuit 774 of FIG. 16. Control begins at 1504, where control determines whether the Telemetry_On signal is present. If so, control transfers to 1508; otherwise, control remains at 1504. At 1508, control determines whether the Telemetry_Power signal is present. If so, indicating that the battery voltage is insufficient for telemetry, control transfers to 1512; otherwise, control returns to 1504. At 1512, control turns off telemetry and continues at 1516. Control remains at 1516 until the Telemetry_Power signal is no longer present, indicating that the battery voltage has recovered. At that point, control transfers to 1520, where telemetry is turned on and control returns to 1504.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. An implantable infusion control device comprising:
   a charge storage unit;
   a pump actuator circuit configured to actuate a pump using energy from the charge storage unit;
   a voltage boost circuit configured to generate a boosted battery voltage from a battery voltage provided by a battery;
   a charging circuit configured to supply a current to the charge storage unit; and
   a selection circuit configured to alternately connect:
      the charging circuit to the battery voltage, bypassing the voltage boost circuit; and
      the charging circuit to the boosted battery voltage,
   wherein the selection circuit is configured to switch between the boosted battery voltage and the battery voltage in response to (i) a comparison of the battery voltage with a predetermined threshold and (ii) a comparison of a voltage of the charge storage unit with the battery voltage.

2. An implantable infusion device comprising:
   the implantable infusion control device of claim 1;
   the pump; and
   the battery.

3. The implantable infusion control device of claim 1 further comprising a charge monitor circuit configured to generate a signal in response to a voltage of the charge storage unit exceeding a predetermined level, wherein the pump actuator circuit is enabled in response to the signal.

4. The implantable infusion control device of claim 1 further comprising:
   a voltage rail configured to be selectively connected to the battery;
   an isolation circuit configured to isolate the voltage rail from the battery voltage in response to a difference between the battery voltage and a voltage of the voltage rail exceeding a threshold; and
   a hold monitor circuit configured to:
      monitor the voltage of the voltage rail;
      in response to the voltage of the voltage rail decreasing below a first threshold, activate the voltage boost circuit;
      in response to the voltage of the voltage rail decreasing below the first threshold, connect the boosted battery voltage to the voltage rail; and
      in response to the voltage of the voltage rail increasing above a second threshold, disconnect the boosted battery voltage from the voltage rail and deactivate the voltage boost circuit,
   wherein the second threshold is greater than the first threshold.

5. An implantable infusion device comprising:
   a pump;
   a charge storage unit;
   a charging circuit configured to supply a first current to the charge storage unit from a battery in preparation for actuating the pump;
   a pump actuator circuit configured to actuate the pump using energy from the charge storage unit;
   a voltage boost circuit configured to provide a boosted battery voltage generated from the battery; and
   a selection circuit configured to, in response to a selection input, alternately connect (i) the voltage boost circuit to the charging circuit or (ii) the battery to the charging circuit, bypassing the voltage boost circuit, wherein the selection input is generated in response to (i) a comparison of a voltage of the battery with a predetermined threshold and (ii) a comparison of a voltage of the charge storage unit with the voltage of the battery.

6. The implantable infusion device of claim 5 wherein the pump comprises a piston and a solenoid coil, and wherein the pump actuator circuit is configured to supply a second current to the solenoid coil from the charge storage unit.

7. The implantable infusion device of claim 5 wherein the predetermined threshold is controlled in response to a firmware setting.

8. The implantable infusion device of claim 5 wherein the comparison of the voltage of the charge storage unit with the voltage of the battery includes comparing the voltage of the charge storage unit to a predetermined percentage of the voltage of the battery.

9. The implantable infusion device of claim 8 wherein the predetermined percentage is controlled in response to a firmware setting.

10. The implantable infusion device of claim 5 further comprising a charge monitor circuit configured to generate a signal in response to a comparison of the voltage of the charge storage unit with a predetermined level, wherein the pump actuator circuit is enabled based on the signal.

11. The implantable infusion device of claim 5 wherein the charging circuit is configured to decrease the first current supplied to the charge storage unit in response to the voltage of the battery decreasing below a second predetermined threshold that is less than the predetermined threshold.

12. The implantable infusion device of claim 11 wherein the charging circuit is configured to, in response to the voltage of the battery decreasing below the second predetermined threshold, halt supplying the first current to the charge storage unit.

13. The implantable infusion device of claim 12 wherein the charging circuit is configured to, after halting supplying the first current to the charge storage unit, begin supplying increasing levels of the first current to the charge storage unit and verifying that the voltage of the battery does not decrease below the second predetermined threshold.

14. The implantable infusion device of claim 5 further comprising:
a voltage rail that is selectively connected to the battery; and
a hold monitor circuit configured to monitor a voltage of the voltage rail and, in response to the voltage of the voltage rail decreasing below a first threshold, activate the voltage boost circuit.

15. The implantable infusion device of claim 14 further comprising an isolation circuit that isolates the voltage rail from the voltage of the battery in response to a difference between the voltage of the battery and the voltage of the voltage rail.

16. The implantable infusion device of claim 14 wherein, in response to the voltage of the voltage rail decreasing below the first threshold, the hold monitor circuit connects the boosted battery voltage to the voltage rail.

17. The implantable infusion device of claim 16 wherein in response to the voltage of the voltage rail increasing above a second threshold that is greater than the first threshold, the hold monitor circuit disconnects the boosted battery voltage from the voltage rail and deactivates the voltage boost circuit.

18. The implantable infusion device of claim 5 further comprising a boost control circuit configured to (i) control the voltage boost circuit and (ii) inhibit operation of the charging circuit while the voltage boost circuit is starting.

19. The implantable infusion device of claim 18 wherein the boost control circuit is configured to inhibit operation of an alarm circuit and a telemetry circuit while the voltage boost circuit is starting.

20. The implantable infusion device of claim 5 further comprising an electronic port finder circuit powered by the charging circuit, wherein the charging circuit is configured such that supplying the first current to the charge storage unit is mutually exclusive with powering the electronic port finder circuit.

21. The implantable infusion device of claim 5 further comprising an alarm circuit configured to generate an audible alarm, wherein the alarm circuit is powered by the voltage boost circuit.

22. The implantable infusion device of claim 21 wherein the alarm circuit disables the charging circuit while the alarm circuit is generating the audible alarm.

23. The implantable infusion device of claim 5 further comprising a telemetry circuit that communicates with an external device, wherein operation of the telemetry circuit is inhibited while the voltage boost circuit is starting.

24. The implantable infusion device of claim 23 wherein the telemetry circuit is configured to shut down in response to the voltage of the battery decreasing below a second predetermined threshold that is less than the predetermined threshold.

25. An implantable infusion device comprising:
a pump that includes a solenoid coil;
a charge storage unit;
a charging circuit configured to supply a first current to the charge storage unit from a battery in preparation for actuating the pump;
a pump actuator circuit configured to supply a second current to the solenoid coil from the charge storage unit;
a charge monitor circuit configured to generate a signal in response to a voltage of the charge storage unit exceeding a predetermined level, wherein the pump actuator circuit is enabled in response to the signal;
a voltage boost circuit configured to provide a boosted battery voltage generated from the battery; and
a boost control circuit configured to inhibit operation of the charging circuit while the voltage boost circuit is starting,
wherein the charging circuit is configured to:
supply the first current to the charge storage unit from the voltage boost circuit instead of directly from the battery in response to (i) a comparison of a voltage of the battery with a predetermined threshold and (ii) a comparison of the voltage of the charge storage unit with a predetermined percentage of the voltage of the battery;
decrease the first current supplied to the charge storage unit in response to the voltage of the battery decreasing below a second predetermined threshold, wherein the second predetermined threshold is less than the predetermined threshold;
in response to the voltage of the battery decreasing below the second predetermined threshold, halt supplying the first current to the charge storage unit; and
after halting supplying the first current to the charge storage unit, (i) begin supplying increasing levels of the first current to the charge storage unit and (ii) verify that the voltage of the battery does not decrease below the second predetermined threshold.

26. The implantable infusion device of claim 25 further comprising:
- a voltage rail configured to be selectively connected to the battery;
- an isolation circuit configured to isolate the voltage rail from the voltage of the battery in response to a difference between the voltage of the battery and a voltage of the voltage rail exceeding a threshold; and
- a hold monitor circuit configured to:
    - monitor the voltage of the voltage rail;
    - in response to the voltage of the voltage rail decreasing below a first threshold, activate the voltage boost circuit;
    - in response to the voltage of the voltage rail decreasing below the first threshold, connect the boosted battery voltage to the voltage rail; and
    - in response to the voltage of the voltage rail increasing above a second threshold, disconnect the boosted battery voltage from the voltage rail and deactivate the voltage boost circuit,
- wherein the second threshold is greater than the first threshold.

* * * * *